United States Patent
Becker et al.

(10) Patent No.: US 11,001,640 B2
(45) Date of Patent: May 11, 2021

(54) METHODS FOR GENERATING BISPECIFIC SHARK VARIABLE ANTIBODY DOMAINS AND USE THEREOF

(71) Applicant: Merck Patent GmbH, Darmstadt (DE)

(72) Inventors: Stefan Becker, Darmstadt (DE); Bjoern Hock, Maintal (DE); Stefan Zielonka, Lorsch (DE); Harald Kolmar, Mühltal (DE); Martin Empting, Muehlheim am Maim (DE)

(73) Assignee: Merck Patent GmbH, Darmstadt (DE)

(*) Notice: Subject to any disclaimer, the term of this patent is extended or adjusted under 35 U.S.C. 154(b) by 1044 days.

(21) Appl. No.: 15/523,888

(22) PCT Filed: Oct. 21, 2015

(86) PCT No.: PCT/EP2015/002086
§ 371 (c)(1),
(2) Date: May 2, 2017

(87) PCT Pub. No.: WO2016/070959
PCT Pub. Date: May 12, 2016

(65) Prior Publication Data
US 2018/0171020 A1    Jun. 21, 2018

(30) Foreign Application Priority Data
Nov. 3, 2014 (EP) .................................. 14003700

(51) Int. Cl.
*A61K 39/00* (2006.01)
*C07K 16/30* (2006.01)
*C07K 16/00* (2006.01)
*C12N 15/81* (2006.01)
*A61K 39/395* (2006.01)

(52) U.S. Cl.
CPC .............. *C07K 16/30* (2013.01); *C07K 16/00* (2013.01); *C12N 15/81* (2013.01); *A61K 39/39558* (2013.01); *A61K 2039/505* (2013.01); *C07K 2317/24* (2013.01); *C07K 2317/31* (2013.01); *C07K 2317/565* (2013.01); *C07K 2317/569* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2013/0302250 A1    11/2013  Barelle et al.
2016/0176951 A1*    6/2016  Barelle .............. C07K 16/2803
                                            424/158.1

FOREIGN PATENT DOCUMENTS

WO    WO-2002/094852 A2    11/2002

OTHER PUBLICATIONS

Alivisatos AP, (1996), 'Perspectives on the Physical Chemistry of Semiconductor Nanocrystals,' J Phys Chem, 100(31):13226-39.
Alivisatos AP, (1996), 'Semiconductor Clusters, Nanocrystals, and Quantum Dots,' Science, 271(5251):933-7.
Altschul SF and Erickson BW, (1986), 'Optimal Sequence Alignment Using Affine Gap Costs,' Bull Math Biol, 48(5/6):603-16.
Barelle C et al., (2009), 'Shark Novel Antigen Receptors—The Next Generation of Biologic Therapeutics?,' Adv Exp Med Biol, 655:49-62.
Benatuil L et al., (2010), 'An Improved Yeast Transformation Method for the Generation of Very Large Human Antibody Libraries,' Protein Eng Des Sel, 23(4):155-9.
Clynes RA et al., (2000), 'Inhibitory Fc Receptors Modulate in vivo Cytotoxicity Against Tumor Targets,' Nat Med, 6(4):443-6.
Database Protein—NCBI, 'Green Fluorescent Protein [unidentified],' Database Accession No. CAA65278.1, Mar. 4, 2000 (4 pages) XP-002752447.
Dooley H et al., (2006), 'First Molecular and Biochemical Analysis of in vivo Affinity Maturation in a Ectothermic Vertebrate,' Proc Natl Acad Sci USA, 103(6):1846-51.
Enever C et al., (2009), 'Next Generation Immunotherapies—Honing the Magic Bullet,' Curr Opin Biotechnol, 20(4):405-11.
Engberg J et al., (1996), 'Phage-Display Libraries of Murine and Human Antibody Fab Fragments,' Mol Biotechnol, 6(3):287-310.
Ferrara C et al., (2006), 'Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-Mannosidase II,' Biotechnol Bioeng, 93(5):851-61.
Garber K, (2014), 'Bispecific Antibodies Rise Again,' Nat Rev Drug Discov, 13(11):799-801.
Gaytán P et al., (1998), 'Combination of DMT-Mononucleotide and Fmoc-Trinucleotide Phosphoramidites in Oligonucleotide Synthesis Affords an Automatable Condon-Level Mutagenesis Method,' Chem Biol, 5(9):519-27.
Greenberg AS et al., (1995), 'A New Antigen Receptor Gene Family that Undergoes Rearrangement and Extensive Somatic Diversification in Sharks,' Nature, 374(6518):168-73.
Hamers-Casterman C et al., (1993), 'Naturally Occurring Antibodies Devoid of Light Chains,' Nature, 363(6428):446-8.
Henikoff S and Henikoff JG, (1992), 'Amino Acid Substitution Matrices from Protein Blocks,' Proc Natl Acad Sci USA, 89(22):10915-9.

(Continued)

*Primary Examiner* — Christopher M Gross
(74) *Attorney, Agent, or Firm* — Goodwin Procter LLP

(57) ABSTRACT

The present invention provides a method for generating bispecific shark variable antibody domains (vNAR domains) and uses thereof. The present invention further provides fusion proteins comprising the inventive bispecific vNAR domains as well as polynucleotide libraries for use in the generation of the inventive bi-specific vNARs. Furthermore, the invention provides pharmaceutical compositions comprising the inventive bispecific vNARs or fusion proteins comprising bi-specific vNAR domains for use in the treatment of pathological conditions in an individual. The invention also provides kits of parts comprising the bispecific vNAR domains or fusion proteins.

9 Claims, 10 Drawing Sheets

Specification includes a Sequence Listing.

(56) References Cited

OTHER PUBLICATIONS

Holz J-B, (2012), 'The TITAN Trial—Assessing the Efficacy and Safety of an Anti-von Willebrand Factor Nanobody in Patients with Acquired Thrombotic Thrombocytopenic Purpura,' Transfus Apher Sci, 46(3):343-6.
International Search Report for International Patent Application No. PCT/EP2015/002086 dated Jan. 26, 2016 (6 pages).
Jefferis R et al., (1998), 'IgG-Fc-Mediated Effector Functions: Molecular Definition of Interaction Sites for Effector Ligands and the Role of Glycosylation,' Immunol Rev, 163:59-76.
Kontermann RE, (2012), 'Dual Targeting Strategies with Bispecific Antibodies,' MAbs, 4(2):182-97.
Kovalenko O et al., (2013), 'Atypical Antigen Recognition Mode of a Shark Immunoglobulin New Antigen Receptor (IgNAR) Variable Domain Characterized by Humanization and Structural Analysis,' J Biol Chem, 288(24):17408-19.
Kovaleva M et al., (2014), 'Shark Variable New Antigen Biologics—A Novel Technology Platform for Therapeutic Drug Development,' Expert Opin Biol Ther, 14(10):1527-39.
Li T et al., (2012), 'Cell-Penetrating Anti-GFAP VHH and Corresponding Fluorescent Fusion Protein VHH-GFP Spontaneously Cross the Blood-Brain Barrier and Specifically Recognize Astrocytes: Application to Brain Imaging,' FASEB J, 26(10):3969-79.
Lifely et al., (1995), "Glycosylation and biological activity of CAMPATH-1H expressed in different cell lines and grown under different conditions," *Glycobiology*, 5(8):813-22.
Liu JL et al., (2007), 'Selection of Cholera Toxin Specific IgNAR Single-Domain Antibodies from a Naïve Shark Library,' Mol Immunol, 44(7):1775-83.
Löfblom J et al., (2011), 'Non-Immunoglobulin Based Protein Scaffolds,' Curr Opin Biotechnol, 22(6):843-8.
Mazutis L et al., (2013), 'Single-Cell Analysis and Sorting Using Droplet-Based Microfluids,' Nat Protoc, 8(5):870-91.
Monroy-Lagos O et al., (2006), 'Improvement of an Unusual Twin-Arginine Transporter Leader Peptide by a Codon-Based Randomization Approach,' Appl Environ Microbiol, 72(5):3797-801.
Mordent J et al., (1999), 'Comparisons of the Intraocular Tissue Distribution, Pharmacokinetics, and Safety of 125I-Labeled Full-Length and Fab Antibodies in Rhesus Monkeys Following Intravitreal Administration,' Toxicol Pathol, 27(5):536-44.
Müller MR et al., (2012), 'Improving the Pharmacokinetic Properties of Biologics by Fusion to an Anti-HAS Shark VNAR Domain,' MAbs, 4(6):673-85.
Needleman SB and Wunsch CD, (1970), 'A General Method Applicable to the Search for Similarities in the Amino Acid Sequence of Two Proteins,' J Mol Biol, 48(3):443-53.
Niwa R et al., (2005), 'IgG Subclass-Independent Improvement of Antibody-Dependent Cellular Cytotoxicity by Fucose Removal from Asn297-Linked Oligosaccharides,' J Immunol Methods, 306(1-2):151-60.
Ohtani M et al., (2013), 'Variable Domain Antibodies Specific for Viral Hemorrhagic Septicemia Virus (VHSV) Selected from a Randomized IgNAR Phage Display Library,' Fish Shellfish Immunol, 34:724-8.

Pearson WR and Lipman DJ, (1988), 'Improved Tools for Biological Sequence Comparison,' Proc Natl Acad Sci USA, 85(8):2444-8.
Pearson WR, (1990), 'Rapid and Sensitive Sequence Comparison with FASTP and FASTA,' Methods Enzymol, 183:63-98.
Rakestraw JA et al., (2011), 'Secretion-and-Capture Cell-Surface Display for Selection of Target-Binding Proteins,' Protein Eng Des Sel, 24(6):525-30.
Rumfelt LL et al., (2004), 'Diversity and Repertoire of IgW and IgM VH Families in the Newborn Nurse Shark,' BMC Immunol, 5:8 (15 pages).
Rumfelt LL et al., (2004), 'Unprecedented Multiplicity of Ig Transmembrane and Secretory mRNA Forms in the Cartilaginous Fish,' J Immunol, 173(2):1129-39.
Sellers PH, (1974), 'On the Theory and Computation of Evolutionary Distances,' SIAM J Appl Math, 26(4):787-93.
Shao C-Y et al., (2006), 'Rapid Isolation of IgNAR Variable Single-Domain Antibody Fragments from a Shark Synthetic Library,' Mol Immunol, 44(4):656-65.
Shields RL et al., (2001), 'High Resolution Mapping of the Binding Site on Human IgG1 for FcγRI, FcγRII, FcγRIII, and FcRn and Design of IgG1 Variants with Improved Binding to the FcγR*,' J Biol Chem, 276(9):6591-604.
Shinkawa T et al., (2003), 'The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity,' J Biol Chem, 278(5):3466-73.
Simmons DP et al., (2006), 'Dimerisation Strategies for Shark IgNAR Single Domain Antibody Fragments,' J Immunol Methods, 315(1-2):171-84.
Stadlmann J et al., (2008), 'Analysis of Immunoglobulin Glycosylation by LC-ESI-Ms of Glycopeptides and Oligosaccharides,' Proteomics, 8(14):2858-91.
Stanfield RL et al., (2004), 'Crystal Structure of a Shark Single-Domain Antibody V Region in Complex with Lysozyme,' Science, 305(5691):1770-1773.
Streltsov VA et al., (2004), 'Structural Evidence for Evolution of Shark Ig New Antigen Receptor Variable Domain Antibodies from a Cell-Surface Receptor,' Proc Natl Acad Sci USA, 101(34):12444-9.
Weller H, (1993), 'Colloidal Semiconductor Q-Particles: Chemistry in the Transition Region Between Solid State and Molecules,' Angew Chem Int Ed Engl, 32(1):41-53.
Wright A and Morrison SL, (1997), 'Effect of Glycosylation on Antibody Function: Implications for Genetic Engineering,' Trends Biotechnol, 15(1):26-32.
Written Opinion for International Patent Application No. PCT/EP2015/002086 dated Jan. 26, 2016 (7 pages).
Wysocki LJ and Sato VL, (1978), '"Panning" for Lymphocytes: A Method for Cell Selection,' Proc Natl Acad Sci USA, 75(6):2844-8.
Yamane-Ohnuki N et al., (2004), 'Establishment of FUT8 Knockout Chinese Hamster Ovary Cells: An Ideal Host Cell Line for Producing Completely Defucosylated Antibodies with Enhanced Antibody-Dependent Cellular Cytotoxicity,' Biotechnol Bioeng, 87(5):614-22.
Zielonka S et al., (2014), '*Shark Attack*: High Affinity Binding Proteins Derived from Shark vNAR Domains by Stepwise in vitro Affinity Maturation,' J Biotechnol, 191:236-45.

* cited by examiner

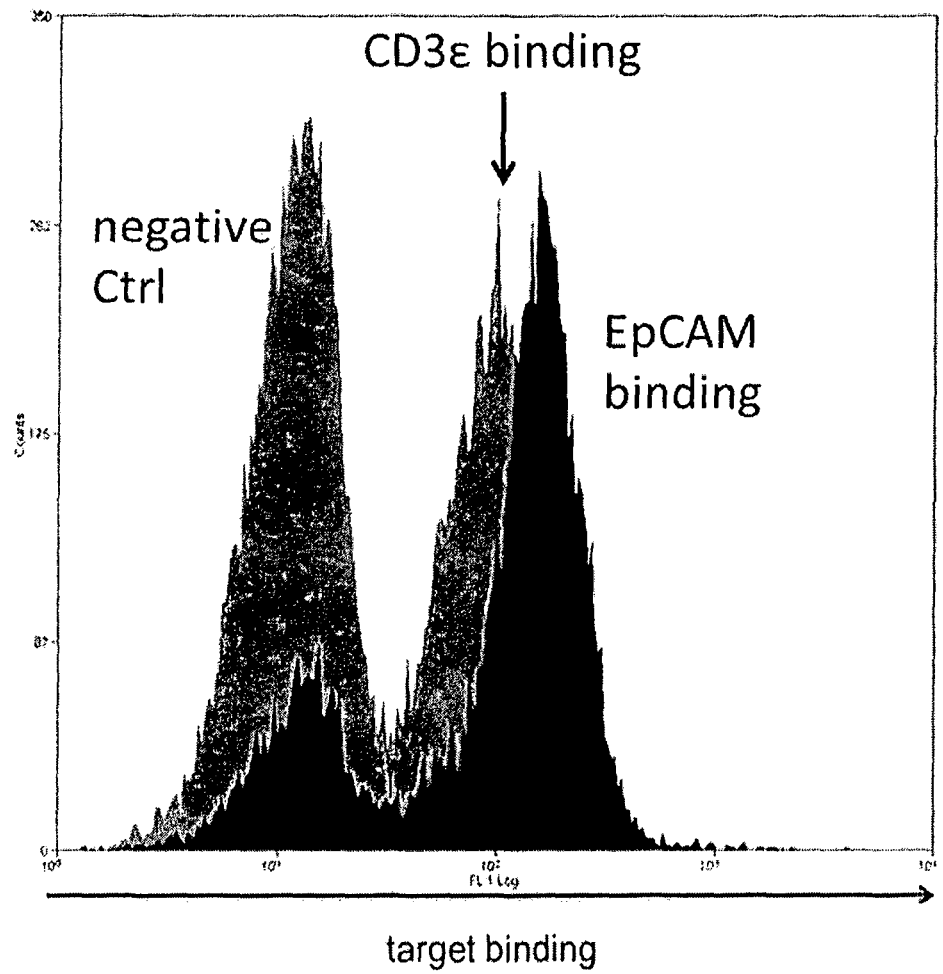

Fig. 7

```
clone B1       1   MAARLEQTPTTTTKEAGESLTINCVLKPEWTILGRTYWYFTKKGTAFKIGKWMGGRYSDT   60
                   MAARLEQTPTTTTKEAGESLTINCVLKPEWTILGRTYWYFTKKG   K      GGRYSDT
parental 5005  1   MAARLEQTPTTTTKEAGESLTINCVLKPEWTILGRTYWYFTKKGATKKARLSPGGRYSDT   60 clone B1       61  KNTASKSLSLRISDLRVEDSGTYHCEALIYSDMGMIMWKIEGGGTTVTVK   110
                   KNTASKSLSLRISDLRVEDSGTYHCEALIYSDMGMIMWKIEGGGTTVTVK
parental 5005  61  KNTASKSLSLRISDLRVEDSGTYHCEALIYSDMGMIMWKIEGGGTTVTVK   110
```

Fig. 8

SEQUENCE LISTING

<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Oligonucleotide for randomization of HV2 domain
<220> FEATURE:
<221> NAME/KEY: modified_base
<222> LOCATION: (1)..(27)
<223> OTHER INFORMATION: a, c, t, g
<220> FEATURE:
<221> NAME/KEY: misc_feature
<222> LOCATION: (1)..(3)
<223> OTHER INFORMATION: First codon (nnn) may be any codon except TGT,
      TGC, for which in 50% one of the codons TTA, TTG, CTT, CTC, CTA,
      CTG may be present
<220> FEATURE:
<221> NAME/KEY: misc_feature
<222> LOCATION: (4)..(24)
<223> OTHER INFORMATION: Any codon may be present except for TAA, TGA,
      TAG
<220> FEATURE:
<221> NAME/KEY: misc_feature
<222> LOCATION: (25)..(27)
<223> OTHER INFORMATION: Last codon (nnn) may be any codon except TGT,
      TGC, for which in 50% one of the codons ACT, ACC, ACA, ACG may be
      present

<400> SEQUENCE: 1 nnnnnnnnn nnnnnnnnn nnnnnnn                                          27

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: vNAR clone B1 amino acid sequence

<400> SEQUENCE: 2

Met Ala Ala Arg Leu Glu Gln Thr Pro Thr Thr Thr Thr Lys Glu Ala
1               5                   10                  15

Gly Glu Ser Leu Thr Ile Asn Cys Val Leu Lys Pro Glu Trp Thr Ile
            20                  25                  30

Leu Gly Arg Thr Tyr Trp Tyr Phe Thr Lys Lys Gly Thr Ala Phe Lys
        35                  40                  45

Ile Gly Lys Trp Met Gly Gly Arg Tyr Ser Asp Thr Lys Asn Thr Ala
    50                  55                  60

Ser Lys Ser Leu Ser Leu Arg Ile Ser Asp Leu Arg Val Glu Asp Ser
65                  70                  75                  80

Gly Thr Tyr His Cys Glu Ala Leu Ile Tyr Ser Asp Met Gly Met Ile
                85                  90                  95

Met Trp Lys Ile Glu Gly Gly Gly Thr Val Thr Val Lys
            100                 105                 110

<210> SEQ ID NO 3
<211> LENGTH: 110
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: Parental vNAR clone 5005

<400> SEQUENCE: 3

Met Ala Ala Arg Leu Glu Gln Thr Pro Thr Thr Thr Lys Glu Ala
1               5                   10                  15

Gly Glu Ser Leu Thr Ile Asn Cys Val Leu Lys Pro Glu Trp Thr Ile
            20                  25                  30

Leu Gly Arg Thr Tyr Trp Tyr Phe Thr Lys Lys Gly Ala Thr Lys Lys
                35                  40                  45

Ala Arg Leu Ser Thr Gly Gly Arg Tyr Ser Asp Thr Lys Asn Thr Ala
    50                  55                  60

Ser Lys Ser Leu Ser Leu Arg Ile Ser Asp Leu Arg Val Glu Asp Ser
65                  70                  75                  80

Gly Thr Tyr His Cys Glu Ala Leu Ile Tyr Ser Asp Met Gly Met Ile
                85                  90                  95

Met Trp Lys Ile Glu Gly Gly Gly Thr Thr Val Thr Val Lys
                100                 105                 110

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: vNAR EphA2-Fc

<400> SEQUENCE: 4

Met Ala Ala Arg Leu Glu Gln Thr Pro Thr Thr Thr Lys Glu Ala
1               5                   10                  15

Gly Glu Ser Leu Thr Ile Asn Cys Val Leu Lys Pro Glu Trp Thr Ile
            20                  25                  30

Leu Gly Arg Thr Tyr Trp Tyr Phe Thr Lys Lys Gly Lys Leu Asn Gly
                35                  40                  45

Arg Lys Leu Arg Lys Gly Gly Arg Tyr Ser Asp Thr Lys Asn Thr Ala
    50                  55                  60

Ser Lys Ser Leu Ser Leu Arg Ile Ser Asp Leu Arg Val Glu Asp Ser
65                  70                  75                  80

Gly Thr Tyr His Cys Glu Ala Leu Ile Tyr Ser Asp Met Gly Met Ile
                85                  90                  95

Met Trp Lys Ile Glu Gly Gly Gly Thr Thr Val Thr Val Lys
                100                 105                 110

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: EphA2_4_Fc

<400> SEQUENCE: 5

Met Ala Ala Arg Leu Glu Gln Thr Pro Thr Thr Thr Lys Glu Ala
1               5                   10                  15

Gly Glu Ser Leu Thr Ile Asn Cys Val Leu Lys Pro Glu Trp Thr Ile
            20                  25                  30
```

```
Leu Gly Arg Thr Tyr Trp Tyr Phe Thr Lys Lys Gly Thr Arg Arg Leu
        35                  40                  45

Lys Asn Leu Lys Thr Gly Gly Arg Tyr Ser Asp Thr Lys Asn Thr Ala
    50                  55                  60

Ser Lys Ser Leu Ser Leu Arg Ile Ser Asp Leu Arg Val Glu Asp Ser
 65                  70                  75                  80

Gly Thr Tyr His Cys Glu Ala Leu Ile Tyr Ser Met Gly Met Ile Met
                85                  90                  95

Trp Lys Ile Glu Gly Gly Gly Thr Thr Val Thr Val Lys
            100                 105
```

```
<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Biotin-acceptor peptide

<400> SEQUENCE: 6

Gly Leu Asn Asp Ile Phe Glu Ala Gln Lys Ile Glu Trp His Glu
1               5                   10                  15
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: acTEV site

<400> SEQUENCE: 7

Glu Asn Leu Tyr Phe Gln Gly
1               5
```

```
<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Oligonucleotide HV2Rand_up
<220> FEATURE:
<221> NAME/KEY: modified_base
<222> LOCATION: (22)..(47)
<223> OTHER INFORMATION: a, c, t, g
<220> FEATURE:
<221> NAME/KEY: misc_feature
<222> LOCATION: (22)..(24)
<223> OTHER INFORMATION: First codon (nnn) pos 22-24 may be any codon
      except TGT, TGC, for which in 50% one of the codons TTA, TTG, CTT,
      CTC, CTA, CTG may be present
<220> FEATURE:
<221> NAME/KEY: misc_feature
<222> LOCATION: (25)..(44)
<223> OTHER INFORMATION: Degenerate codon (nnn)  25-44 may code for any
      amino acid
<220> FEATURE:
<221> NAME/KEY: misc_feature
<222> LOCATION: (45)..(47)
<223> OTHER INFORMATION: Last degenerate codon (nnn)  pos 45-47 may be
      any codon except except TGT, TGC, for which in 50% one of the
      codons ACT, ACC, ACA, ACG may be present
```

<400> SEQUENCE: 8

```
tggtatttca caaagaaggg cnnnnnnnnn nnnnnnnnnn nnnnnnnggc ggacgatact    60
cggacaca                                                            68
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pCT-Seq-lo

<400> SEQUENCE: 9

```
gcgcgctaac ggaacgaaaa atagaaa                                       27
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pCT-Seq-up

<400> SEQUENCE: 10

```
aggacaatag ctcgacgatt g                                             21
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HV2rand_SOE-lo

<400> SEQUENCE: 11

```
gcccttcttt gtgaaatacc a                                             21
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
His Asp Glu Leu
1
```

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis peptide

<400> SEQUENCE: 13

```
His His His His His
1               5
```

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (45)..(45)
<223> OTHER INFORMATION: Thr or Ala
<220> FEATURE:
<221> NAME/KEY: MOD_RES
<222> LOCATION: (46)..(46)
<223> OTHER INFORMATION: Ala or Thr
<220> FEATURE:
<221> NAME/KEY: MOD_RES
<222> LOCATION: (47)..(47)
<223> OTHER INFORMATION: Phe or Lys
<220> FEATURE:
<221> NAME/KEY: MOD_RES
<222> LOCATION: (49)..(49)
<223> OTHER INFORMATION: Ile or Ala
<220> FEATURE:
<221> NAME/KEY: MOD_RES
<222> LOCATION: (50)..(50)
<223> OTHER INFORMATION: Gly or Arg
<220> FEATURE:
<221> NAME/KEY: MOD_RES
<222> LOCATION: (51)..(51)
<223> OTHER INFORMATION: Lys or Leu
<220> FEATURE:
<221> NAME/KEY: MOD_RES
<222> LOCATION: (52)..(52)
<223> OTHER INFORMATION: Trp or Ser
<220> FEATURE:
<221> NAME/KEY: MOD_RES
<222> LOCATION: (53)..(53)
<223> OTHER INFORMATION: Met or Thr

<400> SEQUENCE: 14

Met Ala Ala Arg Leu Glu Gln Thr Pro Thr Thr Thr Thr Lys Glu Ala
1               5                   10                  15

Gly Glu Ser Leu Thr Ile Asn Cys Val Leu Lys Pro Glu Trp Thr Ile
            20                  25                  30

Leu Gly Arg Thr Tyr Trp Tyr Phe Thr Lys Lys Gly Xaa Xaa Xaa Lys
        35                  40                  45

Xaa Xaa Xaa Xaa Xaa Gly Gly Arg Tyr Ser Asp Thr Lys Asn Thr Ala
    50                  55                  60

Ser Lys Ser Leu Ser Leu Arg Ile Ser Asp Leu Arg Val Glu Asp Ser
65                  70                  75                  80

Gly Thr Tyr His Cys Glu Ala Leu Ile Tyr Ser Asp Met Gly Met Ile
                85                  90                  95

Met Trp Lys Ile Glu Gly Gly Gly Thr Thr Val Thr Val Lys
            100                 105                 110

METHODS FOR GENERATING BISPECIFIC SHARK VARIABLE ANTIBODY DOMAINS AND USE THEREOF

This application is a U.S. National Stage Application filed under 35 U.S.C. § 371 of International Patent Application No. PCT/EP2015/002086, filed Oct. 21, 2015, which claims priority to and the benefit of European Patent Application No. 14003700.3, filed Nov. 3, 2014, the contents of each of which are incorporated by reference herein.

SEQUENCE LISTING

The instant application contains a Sequence Listing which has been submitted electronically in ASCII format and is hereby incorporated by reference in its entirety. Said ASCII copy, created on Oct. 5, 2017, is named MRK-012_SL.txt and is 9,941 bytes in size.

FIELD OF THE INVENTION

The present invention concerns the generation of bi-specific shark variable antibody (vNAR) domains and uses thereof. In particular, the present invention concerns the methods for generating and screening of polynucleotide libraries of randomized vNAR domains to identify vNARs of desired phenotype. The inventive method is particularly useful for generating novel bi-specific antibodies and their use.

BACKGROUND OF THE INVENTION

Today biological entities are one of the main drivers of the pharmaceutical industry as exemplified by their current and predicted market growth rates that significantly exceed those of the overall sector. Within this group of biologic drugs, monoclonal antibodies (mAbs) are the highest selling class of biologics, followed by hormones, growth factors and fusion proteins, respectively. The high specificity for a cognate antigen combined with Fc-mediated immune effector functions have underpinned the success of antibodies as effective tools for medical applications. With a number of about 40 US Food and Drug Administration (FDA)—approved antibodies to date and with several hundred mAbs in clinical development, the therapeutic and economic value of mAbs is evident.

IgG-type antibodies are structurally complex, large hetero-tetrameric proteins with a molecular weight of about 150 kD. IgG-type antibodies are comprised of two heavy chains and two light chains. The two identical antigen-binding sites i.e. paratopes, are composed of one variable domain of the light chain and one variable domain of the heavy chain, respectively.

The CH2 domain of the Fc fragment of IgG molecules contains glycans linked via N-glycosylation which are highly heterogeneous, because of the presence of different terminal sugars. Fc glycans influence the binding of IgG to Fc receptors and C1q, and are therefore important for IgG effector functions. Specifically, terminal sugars such as sialic acids, core fucose, bisecting N-acetylglucosamine, and mannose residues affect the binding of IgG to the FcγRIIIa receptor and thereby influence ADCC activity (see e.g. Stadlmann et al. Proteomics. 2008 July; 8(14):2858-71).

Under certain circumstances, however, the therapeutic and diagnostic efficacy of antibodies, such as IgG type antibodies may be limited due to their inherent physico-chemcial properties. For example, tissue penetration by classical antibody molecules may be constrained by their large size (see, e.g. Mordenti et al. (1999) Toxicol Pathol 27:536-44), thus limiting their use in diagnostic methods both in vitro as well as in vivo. Furthermore, slow blood clearance of conventional antibodies due to their extended plasma half-life additionally poses a problem for in vivo tumor imaging purposes. Also, non-specific uptake of classical antibodies by healthy tissues further adds to the limitations imposed on their use in molecular imaging.

In an attempt to overcome the above limitations of classical antibodies and to increase their overall therapeutic efficacy so called "next-generation" antibodies or antibody fragments, as well as non-immunoglobulin-based protein scaffolds have been devised. Examples of next-generation antibodies include for instance unibodies, scFv, diabodies, or for example adnectins, affibodies, anticalins, or cysteine-knot proteins (see e.g. Enever et al. (2009) Current Opinion in Biotechnology, Vol 20 (4), 405-411; Löfblöm et al. Curr Opin Biotechnol. 2011 December; 22(6):843-8).

Another class of antibodies which has received much attention over the last years due to their atypical structure is found in camelids and the cartilaginous fish, which possess natural antibodies composed only of heavy chains (see, e.g. Greenberg et al. (1995) Nature 374:168-73; Hamers-Casterman et al. (1993) Nature 363:446-8). In these antibodies, the antigen binding site is formed by only one single domain, referred to as VHH and vNAR, respectively. Due to an increased frequency for polar and charged amino acids at the solvent-exposed regions corresponding to the hydrophobic VH-VL interface of conventional antibodies, vNAR and VHH domains are highly soluble.

Antigen binding domains of heavy chain only antibodies (HCAbs) combine most of the beneficial features of non-immunoglobulin-based protein scaffolds e.g. small size and high stability coupled with the advantageous characteristics of classical antibody molecules, most strikingly the feasibility to generate highly specific and high-affinity binders through immunization. Interestingly, HCAbs naturally complement the conventional repertoire of the aforementioned species: Whereas classical antibodies usually have planar or concave antigen binding sites, vNAR- and VHH-domains possess a wide variety of additional (in the case of vNARs) and different loop structures. This leads to a drastically expanded repertoire of available paratopes capable of accessing and binding to more cryptic epitopes and catalytic clefts of enzymes which are intractable to classical antibodies.

While camelid VHH domains have proven to be successful in early phase clinical trials (see e.g. Holz et al. (2012) Transfus Apher Sci. 2012 June; 46(3):343-6), the engineering of vNAR domains for biomedical applications has not progressed thus far yet. However, significant progress demonstrating the therapeutic utility of these domains has been made in the last years.

Cartilaginous fish (sharks, rays, skates and chimaeras) express three different isotypes of antibodies, IgM, IgNAR and the primordial IgW (Rumfelt L L. et al. BMC immunology 2004; 5:8; Rumfelt L L et al. Journal of immunology 2004; 173:1129-39). IgNAR was first identified in the serum of the nurse shark (*Ginglymostoma cirratum*) (Greenberg A S et al. Nature 1995; 374:168-73). IgNAR is a homodimer of heavy chains devoid of light chains. Each chain of the secretory form consists of one variable domain followed by five constant domains, the last four being homologous to IgW constant domains. Serum IgNAR levels range from approximately 0.1 mg/ml to 1 mg/ml.

Based on atomic resolution structural data as well as small-angle X-ray scattering a structural model of the complete IgNAR molecule was obtained. Within the molecule, domains C1 and C3 of each chain cause dimerization of IgNAR. Despite the lack of a canonical hinge region, the variable domains are spaced sufficiently wide for binding a large variety of epitopes, which is also facilitated by the wide angle of the C1 dimerization interface. A small angle between both C3 domains induces the formation of a narrow stalk for the IgNAR molecule. However, the flexibility of the stalk is induced by a disulfide-bridged linker that connects domains C3 and C4. The heavy chain-only molecule is kinked approximately in the middle of the molecule, at the location of the flexible linker, causing its characteristic shape. Whether any effector functions are mediated by the constant region of IgNAR is currently unresolved.

The homodimer IgNAR displays several unique features that are responsible for the inhibition of a potential light chain pairing. At the typical VH-VL interaction site, there is poor conservation of residues that mediate this association in mammals. Instead these typically hydrophobic amino acids are frequently replaced by polar or charged residues. For classical antibodies, a special mechanism ensures the formation of heavy- and light chain pairing. In the endoplasmic reticulum the heavy chain is trapped by an Ig-binding protein (BiP) via interaction with the CH1 domain. For the release, a light chain must displace BiP. Consequently, only heavy- and light-chain paired antibodies are secreted.

The variable domain of the New Antigen Receptor shows sequence homology to the T-cell receptor (TCR) Vα and also to immunoglobulin $V_K$ domains, whereas structurally it is related to Vα, Vλ, and VH domains. Moreover, since vNAR domains share structural features of cell adhesion molecules it was suggested that IgNAR evolved from a cell-surface receptor clearly distinguishing it from VHH which evidently arose from an IgG lineage. vNAR belongs to the Ig superfamily and accordingly it has an β-sandwich fold. However, compared to mammalian V domains this fold only consists of 8 instead of 10 β-strands, due to the deletion in the framework2-CDR2-region which makes the vNAR domain the smallest antibody-like antigen binding domain in the animal kingdom to date with a molecular mass of approximately 12 kDa (Barelle C et al., Adv Exp Med Biol 2009; 655:49-62; Stanfield R L et al. Science 2004; 305: 1770-3).

As a consequence, contrary to mammalian variable domains, vNAR domains have only two complementary determining regions CDR1 and CDR3. The diversity of the primary vNAR repertoire is predominantly found in CDR3. High rates of somatic mutation after antigen contact are observed in CDR1, at the CDR2 truncation site, where the remaining loop forms a belt-like structure at the bottom of the molecule, and in a loop which corresponds to HV4 in TCRs. Accordingly, these mutation-prone regions have been named HV2 and HV4, respectively (see e.g. Dooley et al., PNAS (USA) 2006; 103:1846-51).

Despite having a reduced number of possible antigen binding loops (four across a single chain) compared to classical antibodies (six loops across two chains), vNAR domains bind antigens with surprisingly high affinities. Even from primary repertoires, where antigen binding is solely mediated by CDR3, vNAR molecules can be raised against a given antigen with affinities in the low nanomolar range. The highest recorded affinities for vNAR domains however, have been observed after immunization with an anti-albumin binding domain known as E06 achieving picomolar levels of affinity (Muller et al., MAbs 2012; 4:673-85).

vNAR molecules have been categorized into four types based on the respective number of non-canonical cysteine residues. All types have the classical Ig canonical cysteines in common, that stabilize the immunoglobulin fold via a disulfide-bond. Type I variable domains carry extra cysteines in framework regions 2 and 4 and consequently, an even number of partner cysteine residues in CDR3. The determination of the crystal structure of a type I vNAR in complex with lysozyme revealed that both non-canonical framework cysteines each form disulfide-bonds with those of CDR3, causing this loop to be held tightly into the direction of HV2. Thus far, type I variable domains of IgNAR have only been identified in the nurse shark, *Ginglymostoma cirratum*.

Type II domains differ from type I by means of an additional cysteine in CDR1 and in CDR3, respectively, resulting in an intra-molecular disulfide bond that brings both loops in close vicinity. However, type II domains lack both cysteine motifs which anchor CDR3 to the framework in type I vNAR. As a consequence, the CDR3 region forms a protrusive 'finger-like' structure that is predisposed to binding into pockets or grooves, e.g. the active site of enzymes.

Type III domains are expressed in neonatal fish. Akin to type II domains, this isotype is characterized by an additional non-canonical cysteine in CDR1 and CDR3, respectively. However, in contrast to type II, type III domains comprise a restricted CDR3 diversity, highly similar in amino acid composition and length as well as a conserved tryptophan residue in CDR1 positioned adjacent to the disulfide bridge between both loops.

Type IV domains differ from all described vNAR types in that they only comprise the canonical disulfide bond. Therefore the topology of the paratope of type IV variable domains is more flexible and not physically constrained. Type IV domains are also referred to as type IIb (Streltsov et al. PNAS 2004; 101:12444-9; Liu et al., Molecular immunology 2007; 44:1775-83).

Type IV domains with an invariant tryptophan residue in CDR1 have been identified thereby displaying some similarity to type III domains. With the exception of type III vNAR domains, all types of the vNAR domains give rise to high-affinity binders.

The use of antibody-based therapies in cancer treatment has become well established in the last 2 decades and is now one of the most successful and important strategies for treating patients with haematological malignancies and solid tumors. The fundamental basis of antibody-based therapy of tumors is the expression of antigens by tumor cells that are overexpressed, mutated or selectively expressed compared with normal tissues.

Most of the monoclonal antibodies (mAbs) approved for marketing in the US target single cell surface antigens, such as e.g. adalimumab (Humira; Abboft/AbbVie), directed against TNFα, panitumumab (Vectibix; Amgen) directed against EGFR, ofatumumab (Arzerra; Genmab) directed against CD20. However, tumor cells often upregulate different growth-promoting receptors that can act either independently or crosstalk intra-cellularly. Targeting of one receptor by a mono-specific antibody may result in resistance which is associated with the upregulation of alternative receptors as well as pathway switching (Kontermann (2012) mAbs 4:2, 182-197), indicating that it may be beneficial to target or block multiple cell surface antigens (targets) on a tumor cell. This has been recognized and there are currently more than 15 bispecific antibodies in clinical trials, i.e. antibodies that target two different cell surface antigens (see e.g. Garber, Nat Rev Drug Discov. 2014 Oct.

31; 13(11):799-801). However, human bispecific antibodies thus far are only able to target planar or concave antigen binding sites, thereby precluding antigen binding sites that may therapeutically more effective.

Thus, in view of the limitations of classical epitopes targeted by human or humanized bispecific antibodies, there is a continued demand for novel and effective bispecific antibody-based cancer therapeutics. It is therefore an object of the present invention to provide novel bispecific antibodies which overcome the current limitations in antigen targeting.

SUMMARY OF THE INVENTION

The present inventors have surprisingly found that bispecific vNAR domains can be obtained by randomizing the amino acid sequence of hypervariable region 2 (HV2) of vNAR types I, II and IV domains. Accordingly, the present invention present invention provides a method for generating bi-specific shark variable antibody domains (vNAR domains) having the structure of FW1-CDR1-FW2-HV2-FW3a-HV4-FW3b-CDR3-FW4, whereby the method comprises the steps of a. randomizing at least one polynucleotide sequence encoding the hypervariable region 2 (HV2),
b. detection of vNAR domains in which HV2 binds to an antigen of interest with altered affinity compared to a reference sample and a second antigen of interest is specifically bound by the paratope formed by CDR3 and CDR1.
c. selecting vNAR domains of (b).

In one embodiment, the vNAR domains which may be randomized by the inventive method are one of vNAR type I, vNAR type II, or vNAR type IV.

In one embodiment, the randomization according to the invention of the polynucleotide coding region of HV2 comprised on at least one polynucleotide encoding said vNAR comprises codon-based randomization, NNB randomization, NNK randomization, NNS randomization, or biased-randomization.

According to one embodiment, the polynucleotide sequence encoding the HV2 domain according to the invention comprises the nucleotide sequence $NNN_1(NNN)_7NNN_9$ (SEQ ID NO: 1), wherein 50% of the codons in position 1 code for the amino acid lysine and the remaining 50% encode any amino acid except cysteine, and Codons 2-8 may encode any amino acid, and 50% of the codons in position 9 code for the amino acid threonine, and the remaining 50% encode any amino acid except cysteine.

In one embodiment, vNARs according to the invention that display an altered affinity to a first antigen compared to a reference sample are detected and/or selected by one of yeast surface display, phage display, mammalian display, or protein array.

According to one embodiment, the vNAR according to the present invention further comprises a detectable tag.

In one embodiment, the detectable tag of the vNAR according to the invention is located at the amino terminus and/or carboxy-terminus of the vNAR.

In one embodiment, the inventive vNARs are detected and/or selected by flow cytometry, FACS, ELISA, or microfluidics.

According to one embodiment, the first and second antigen of interest of the inventive method are cell surface antigens, preferably cancer cell surface antigens.

In one embodiment, the present invention provides a fusion protein comprising the randomized HV2 domain according to the inventive method, or the inventive vNAR domain comprising the randomized HV2 domain according to inventive method.

In one embodiment, the inventive fusion protein comprises one of IgG-Fc domain, VH, VL, VHH antibody domains or fragments thereof.

In one embodiment, the inventive fusion protein is humanized.

In one embodiment, the Fc-domain of inventive fusion protein comprises human IgG-Fc domains, or sequence variants thereof.

According to one embodiment, the inventive fusion protein when bound to said first and said second antigen of interest induces ADCC in vivo.

In one embodiment, the present invention provides a vNAR obtainable by the inventive method.

In one embodiment, the present invention provides for a vector which comprises a polynucleotide sequence encoding the inventive vNAR, or an inventive fusion.

In one embodiment, the present invention provides for a host cell, which comprises the vector according to the invention.

In one embodiment, the present invention provides a method of producing inventive vNAR or vNAR fusion proteins, wherein the method comprises the steps of:

Culturing at least one host cell according to the invention under conditions sufficient for protein expression of the inventive vNAR, or vNAR fusion protein, and Isolating and purifying the inventive vNAR protein, or vNAR fusion protein.

According to one embodiment, the present invention provides for a polynucleotide library, which comprises a plurality of polynucleotides encoding the inventive HV2 domain as disclosed herein.

In one embodiment, the inventive polynucleotide library comprises a plurality of polynucleotides encoding type I, II, or type IV vNAR domains of the overall structure FW1-CDR1-FW2-HV2-FW3a-HV4-FW3b-CDR3-FW4, whereby the HV2 domain is encoded by a randomnized polynucleotide sequence according to the invention.

In one embodiment, the present invention provides bispecific vNAR comprising the amino acid sequence according to SEQ ID NO: 2, SEQ ID NO: 4, SEQ ID NO: 5.

In one embodiment, the present invention pertains to the use of the inventive vNARs, or of the inventive fusion protein in the manufacture of a medicament.

In one embodiment, the present invention provides a pharmaceutical composition comprising the inventive vNAR, or the inventive vNAR fusion proteins as disclosed herein and a pharmaceutical acceptable carrier or diluent.

In one embodiment, the present invention pertains to a method of treating an individual inflicted with pathological condition comprising administering to an individual in need thereof the pharmaceutical composition according to the invention.

In one embodiment, the pathological condition to be treated by the inventive method of is cancer, autoimmune disease, or viral infection.

In one embodiment, the individual to be treated by the inventive method has a tumor.

According to one embodiment, the individual to be treated by the inventive method is a human.

In one embodiment, the invention provides a kit of parts, which comprises the bispecific vNAR or the inventive vNAR fusion protein and means for detecting the inventive vNAR.

BRIEF DESCRIPTION OF THE DRAWINGS

FIG. 7: Validation of bispecificity using yeast surface display. Yeast cells expressing vNAR B1 on their surface incubated with 540 nM EpCAM (black) or 770 nM CD3c or only with secondary detection reagents.

FIG. 8: Sequencing of EpCAM- and CD3ε-specific vNAR molecule B1 (SEQ ID NO: 2) and of its parentalal molecules 5005 (SEQ ID NO: 3) (only EpCAM specific). Randomized residues in HV2 are shown in grey. FIG. 8 also discloses SEQ ID NO: 14.

SEQUENCE LISTING

Figure 1:
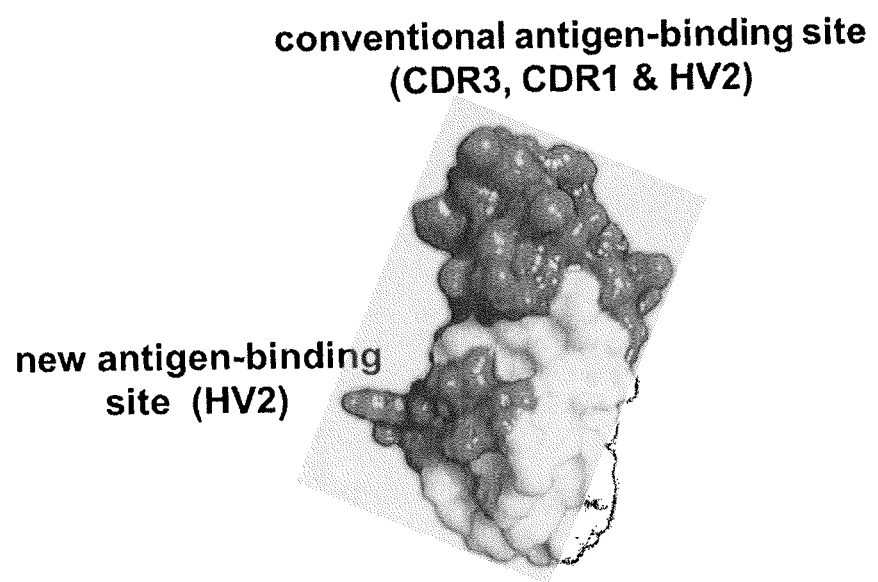
FIG. 1: vNAR molecule showing the conventional paratope (antigen-binding site). A new antigen binding site is introduced via randomization of HV2, resulting in a bispecific molecule, targeting two different antigens.
Figure 2:
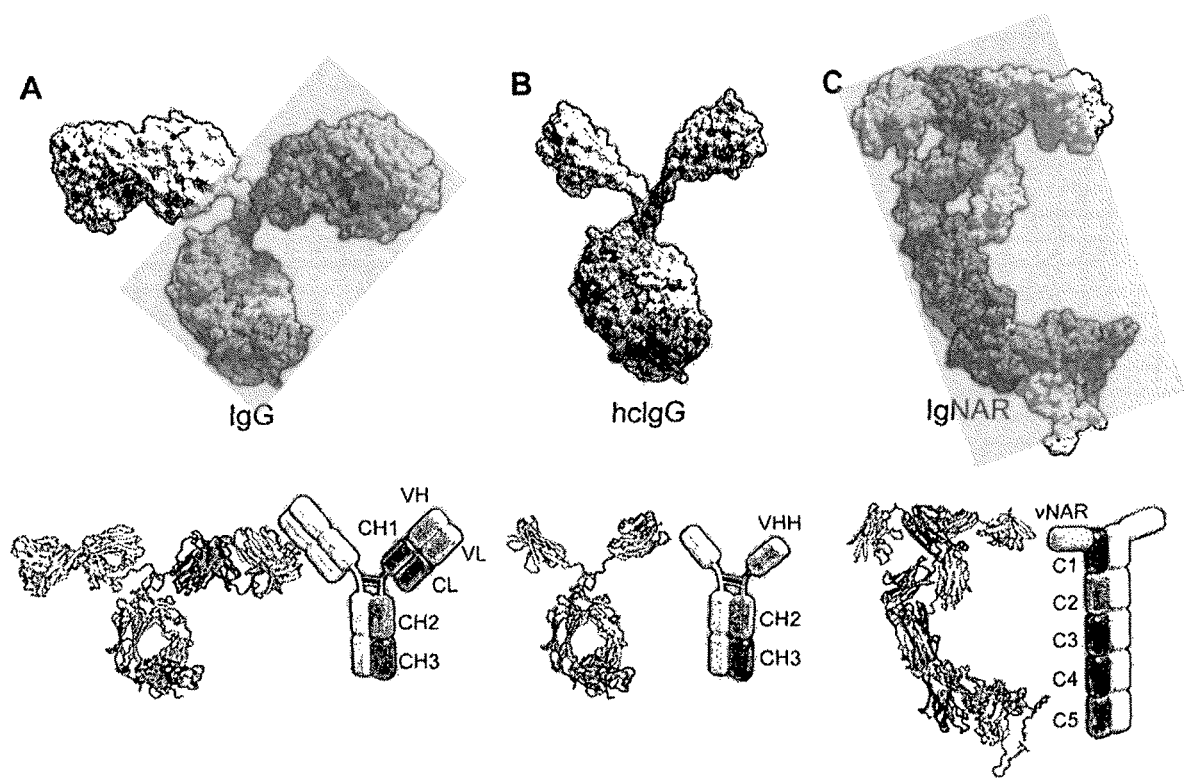
FIG. 2: Antibody structures of various antibody molecules (A) IgG molecule, (B, C) Camelids and the cartilaginous fish antibody molecules, which are naturally only composed only of heavy chains.
Figure 3:
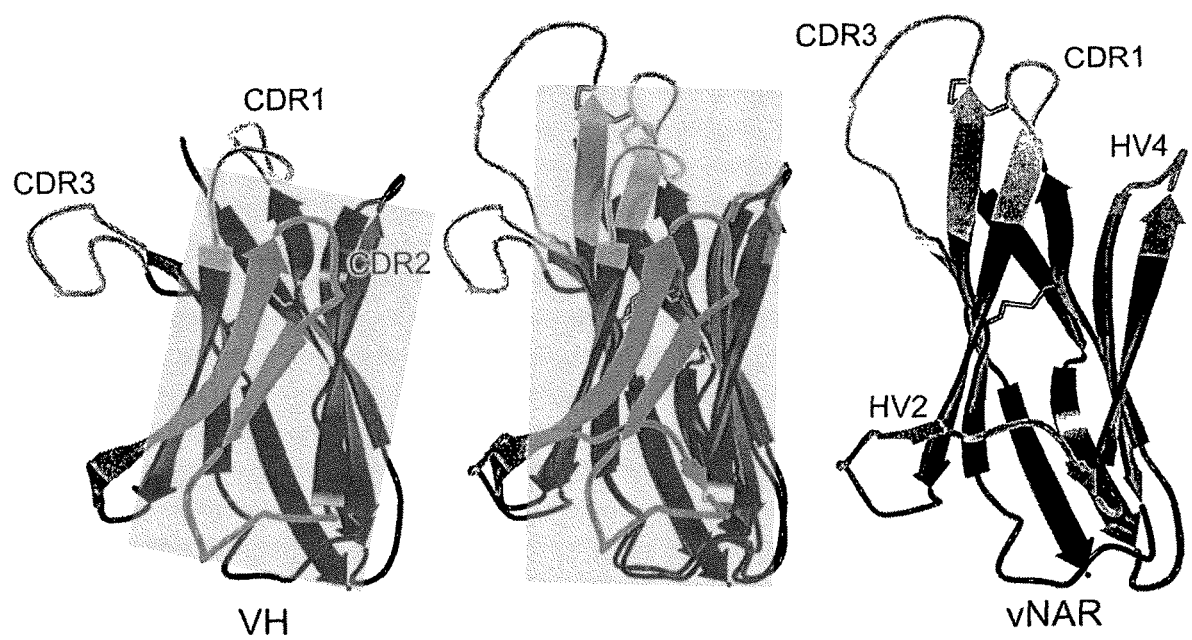
FIG. 3: Comparison of antibody structures: vNARs belong to the Ig superfamily and has an β-sandwich fold, however, compared to mammalian V domains this fold only consists of 8 instead of 10 β-strands, due to the deletion in the framework2-CDR2-region. As a consequence, contrary to mammalian variable domains, vNAR domains have only two complementary determining regions CDR1 and CDR3. The diversity of the primary vNAR repertoire is predominantly found in CDR3. High rates of somatic mutation are observed in CDR1, at the CDR2 truncation site and in a loop which corresponds to HV4 in TCRs. Accordingly, these mutation-prone regions have been named HV2 and HV4, respectively.
Figure 4:
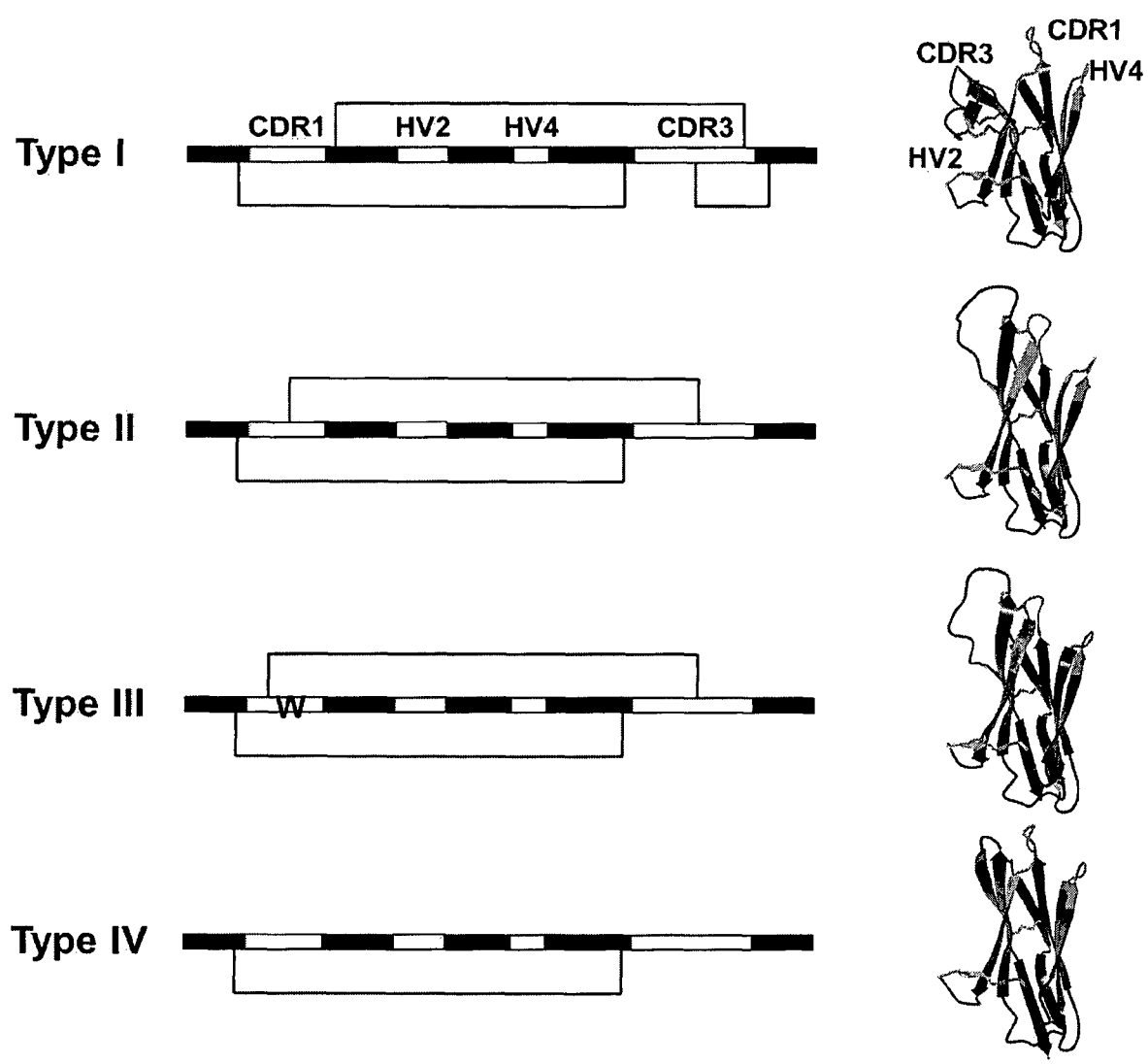
FIG. 4: Different vNAR types known, including type I, type II, type III and type IV.
Figure 5:
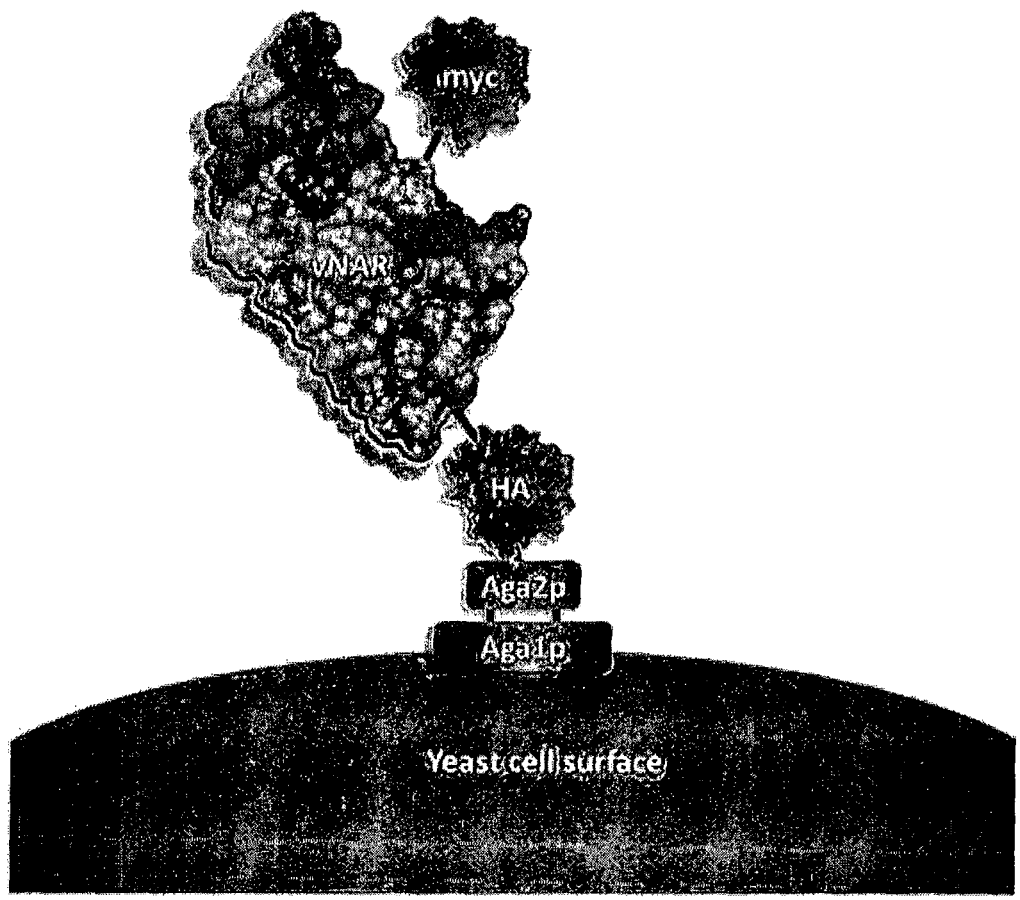
FIG. 5: Illustration of yeast surface display. vNARs are presented on the surface of S. cerevisiae as Aga2p fusions with an N-terminal HA-epitope and a C-terminal cMyc-tag, respectively, for the detection of surface expression.

SEQ ID NO: 1 artificial polynucleotide used for randomization of HV2 domain
SEQ ID NO: 2 amino acid sequence of vNAR clone B1
SEQ ID NO: 3 amino acid sequence of parental vNAR clone 5005
SEQ ID NO: 4 amino acid sequence of vNAR EphA2-Fc
SEQ ID NO: 5 amino acid sequence of vNAR EphA2_4-Fc
SEQ ID NO: 6 amino acid sequence of biotin-acceptor polypeptide
SEQ ID NO: 7 acTEV site
SEQ ID NO: 8 oligonucleotide HV2Rand_up
SEQ ID NO: 9 pCT-Seq-lo
SEQ ID NO: 10 pCT-Seq-up
SEQ ID NO: 11 HV2rand_SOE-lo

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The described objectives are solved by the present invention, preferably by the subject matter of the appended claims. The inventors have surprisingly found that bispecific vNAR domains can be obtained by the inventive method which comprises the steps of (a) randomizing at least one polynucleotide sequence encoding the hypervariable region 2 (HV2), (b) detection of vNAR domains in which HV2 binds to an antigen of interest with altered affinity compared to a reference sample and a second antigen of interest is specifically bound by the paratope formed by CDR3 and CDR1 and (c) selecting vNAR domains of (b). Accordingly, the inventive method comprises randomizing at least one polynucleotide sequence encoding the HV2 domain of at least one vNAR and detecting vNARs which bind to a first antigen of interest with altered affinity compared to a reference sample and a second antigen of interest, which is bound by the paratope formed by CDR1 and CDR3 of the vNAR domain, followed by selecting vNAR domains, which show an altered affinity to a first antigen of interest. The term "vNAR domain" as used in the inventive method refers to the antigen-binding site, which is formed by only one single domain present on IgNAR found in cartilaginous fish, such as e.g. shark, ray and skate, e.g. *Ginglymostoma cirratum*, or *C. plagiosum*, The vNAR domains according to the invention may be vNAR type I, vNAR type II, or vNAR type IV as disclosed above, or e.g. as disclosed in Kovaleva et al. (2014), Expert Opin Biol Ther. October; 14(10):1527-39.

In the inventive method, the first antigen of interest and the second antigen of interest may e.g. cell surface antigens, which e.g. refers to a protein, polypeptide or peptide, where at least one antigenic portion of the protein, polypeptide or peptide is exposed on a surface of a biological membrane and which may have one or more of the following moieties covalently attached: one or more simple or complex sugar moieties (as in a glycoprotein), lipid moieties (as in a lipoprotein), a combination of lipid and sugar moieties, or other post-translational modifications. "Proteins" are typically long chains of amino acid based polymers ("polypeptides"). Proteins may be composed of one, two or more polypeptide chains and may further contain some other type of substance in association with the polypeptide chain(s), such as carbohydrates. The size of proteins covers a rather wide range from (an arbitrary figure of) 5,000 to several hundred thousand g/mole. The term antigen of interest or cell surface antigen as used for the inventive method also includes e.g. receptor tyrosine kinases such as e.g. PDGFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK or MUSK. The antigen of interest in the inventive method may e.g. also comprise glycans, whereby, the term "glycan" refers a compounds consisting of a large number of monosaccharides linked glycosidically. For example, glycans may include glycosaminoglycans, which comprise 2-aminosugars linked in an alternating fashion with uronic acids, and include polymers such as heparin, heparan sulfate, chondroitin, keratin, and dermatan. In the inventive method, the first antigen of interest and second antigen of interest may e.g. be located on the same molecule, or cell surface antigen, or the first and second antigen of interest may be located on two distinct molecules, e.g. the first antigen of interest may be formed by a cell surface protein or protein fragment, while the second antigen of interest may be formed by a non-proteinaceous cell surface antigen, such as a glycan. The first and second antigen of interest of the invention may also be a tumor antigen, or cell surface cancer cell antigen, tumor-associated antigen, or tumor-specific antigens which comprise, for example, any immunogenic epitope expressed by a tumor cell. The protein may be expressed by non-tumor cells but be immunogenic only when expressed by a tumor cell, e.g. due to altered (increased, or decreased) glycosylation. Alternatively, the protein may be expressed by tumor cells or cancer cells, but not normal cells. In one embodiment the tumor antigen, cell surface cancer cell antigen, or tumor-associated antigen, or tumor-specific antigens is a human tumor antigen. For example, tumor antigens may include melanoma-associated Chondroitin Sulfate Proteoglycan (MCSP, UniProt Q6UVK1, NCBI Accession NP 001888), Fibroblast Activation Protein (FAP, Uni Prot Q12884, Q86Z29, Q99998; NCBI Accession NP 004451), Epidermal Growth Factor Receptor (EGFR, also known as ErbBl and Herl, UniProt P00533; NCBI Accession NP_958439, NP_958440), Carcinoembryonic Antigen (CEA, also known asCarcinoembryonic antigen-related cell adhesion molecule 5 or CD66e; UniProt P06731, NCBI Accession NP 004354) and CD33 (also known as gp76 or Sialic acid-binding Ig-like lectin 3 (Siglec-3), UniProt P20138, NCBI Accession NP 001076087, NP 001171079).

As used for the inventive method, the term "altered" or "altered affinity" encompasses changes in the binding constant of a vNAR to one or more antigens of interest, e.g. one, two, three, or four antigens of interest by e.g. the paratope formed by vNAR HV2, or e.g. by the paratope formed by vNAR CDR1 and CDR3. For example altered affinity may encompass reduced, or increased affinity to a given antigen of interest, preferably an increased affinity to the antigen of interest, which may contain linear and/or discontinuous. There is no critical upper limit to the length of the fragment, which may (for example) comprise nearly the full-length of the antigen sequence, or even a fusion protein comprising two or more epitopes from the target antigen. In one embodiment, the altered affinity of the vNAR HV2 domain to a first antigen of interest is at least e.g. $10^{-7}$M, $2.5\times10^{-7}$M, $5\times10^{-7}$M, $7.5\times10^{-7}$M, $1\times10^{-8}$ M, $2.5\times10^{-8}$ M, $5\times10^{-8}$ M, $7.5\times10^{8}$ M, $10^{-9}$M, $2.5\times10^{-9}$M, $5\times10^{-9}$M, $7.5\times10^{-9}$M, $10^{-10}$M, $2.5\times10^{-10}$M, $5\times10^{-10}$M, $7.5\times10^{-10}$M, $10^{-11}$M, $2.5\times10^{-11}$M, $5\times10^{-11}$M, $7.5\times10^{-11}$M, or $10^{-12}$M.

The term randomization as used with the inventive method refers to a process that produces a plurality of sequences where one or several positions have been randomized. In some embodiments, randomization is complete (i.e., all four nucleotides, A, T, G, and C can occur at a randomized position. In alternative embodiments, randomization of a nucleotide is limited to a subset of the four nucleotides. Randomization can be applied to one or several codons of the polynucleotide sequence encoding the hypervariable region 2 (HV2). When expressed, the resulting libraries produce HV2 populations in which one or more amino acid positions can contain a mixture of all 20 amino acids or a subset of amino acids.

In one embodiment the randomization of the polynucleotide sequence encoding HV2 (HV2 coding region) in the inventive method may include codon-based randomization, NNB randomization, NNK randomization, NNS randomization, or biased-randomization. For example, codon-based randomization as used in the inventive method may be done according to the method described by Gaytan et al. (1998) Chemistry&Biology 5:519-527, or according to Monroy-Lagos et al. (2006), APPLIED AND ENVIRONMENTAL MICROBIOLOGY, May 2006, p. 3797-3801). In the inventive method NNB randomization refers to a degenerate codon with 25% of each nucleotide at the first two positions and 33% of C, T, and G at the third position. Tyr/Ser refers to an even mix of tyrosine and serine. For example, "NNK randomization" as used in the inventive method can be used to generate single amino acid variants, where "N" refers to any base (e.g., A, C, G, or T) and "K" refers to either G or T. The NNK randomization scheme can encode 32 different codons covering all 20 naturally occurring amino acids. Amino acid residues at each position of the protein can be mutated to any one of the 19 amino acids that is different than the wild type amino acid at the same position, resulting in single amino acid point mutation along the protein. The end result is a protein variant library encompassing groups of multiple proteins having one residue that varies from member to member in the library.

For example, to reduce the frequency of termination codons in the randomization of the polynucleotide encoding the HV domain of the inventive bispecific vNAR in the inventive method may include NNS randomization, where n denotes the number of random triplets to be included, N represents any nucleotide, and S represents C or G in the standard IUPAC nucleotide nomenclature. Since two of three stop codons (TGA and TAA) have an A in the third position, an NNS strategy is expected to reduce the frequency of stop codons from 3/64 to 1/32 compared to an NNN strategy. The randomization in the inventive method may e.g. also be a biased-randomization, e.g. some positions within the sequence are either held constant, or are selected from a limited number of possibilities. For example, in one embodiment, the first and the last codon of the randomized polynucleotide comprising the HV2 coding region may be subjected to biased-randomization, e.g. the first codon may comprise all codons, except for TGT, TGC and the last codon may be any codon except TGT, TGC, while in 50% of the codons used for the first codon the first codon may be selected from TTA, TTG, CTT, CTC, CTA, CTG and for the second codon may be selected from ACT, ACC, ACA, ACG.

In one embodiment, the polynucleotide sequence encoding the HV2 domain comprises the nucleotide sequence according to SEQ ID NO: 1, which may e.g. be randomized according to any of the randomization techniques disclosed above. Preferably, the first codon of the polynucleotide according to the invention may in 50% of the polynucleotides code for the amino acid lysine, e.g. the codons are selected from AAA, or AAG in 50% of the polynucleotides, while in 50% of the polynucleotides any codon may be present, with the exception of TGT, TGC which code for cysteine. Codons 2-8 of the polynucleotide encoding the HV2 domain according to the invention may code for any amino acid, e.g. any codon may be present except for TAA, TAG or TGA. Codon 9 of the polynucleotide encoding the HV2 domain according to the invention may in 50% of the polynucleotides code for the amino acid threonine, e.g. the codons are selected from ACT, ACC, ACA, or ACG in 50% of the polynucleotides any codon may be present, with the exception of TGT, TGC. For example, the polynucleotide sequence according to SEQ ID NO: 1 may be comprised in an oligonucleotide sequence, such as e.g. the oligonucleotide sequence according to SEQ ID NO: 8, which may be used in a PCR-based technology (e.g. SOE PCR) to generate a polynucleotide library, which comprises or encodes vNAR proteins comprising the randomized HV2 domain.

In one aspect of the invention, vNAR libraries may e.g. be obtained from total RNA from shark as template for cDNA synthesis using e.g. the Omniscript®Reverse Transcription Kit(Qiagen) and OdT-Oligonucleotides. The PCR amplified vNAR products may e.g. be used as starting material for the semi-synthetic library construction. The initial library may be e.g. established in three consecutive PCR-steps (see e.g. in the appended examples, or e.g. Zielonka, S. et al. (2014) Journal of Biotechnology).

In one embodiment, the vNARs of the invention which display an altered affinity to a first antigen compared to a reference sample are detected and/or selected by one of yeast surface display, phage display, mammalian display, or protein array. Accordingly, the inventive method comprises e.g. subjecting the randomized HV2 domain-comprising vNARs to one of yeast surface display, phage display, mammalian display, or protein array. For example, the polynucleotide encoding the vNAR comprising a randomized HV2 domain according to the invention may be subjected to yeast display to detect and select vNARs which have an altered affinity to a first antigen compared to a reference sample. For example, yeast display may be done according to the method as provided by Rakestraw (see Rakestraw (2011) Protein Engineering, Design & Selection Vol. 24, no. 6: 525-530). For example, the at least one polynucleotide encoding the vNAR of the invention may be cloned e.g. into a SECANT vector thereby genetically fusing the inventive vNARs to a biotin-acceptor peptide (BAP: GLNDIFEAQKIEWHE (SEQ ID NO: 6)) via e.g. an acTEV protease site (ENLYFQG (SEQ ID NO: 7)). The vector may e.g. also comprise an operationally linked tag 5' to the vNAR, such as e.g. FLAG tag (Sigma), or a Myc-Tag. 5' to the tag and operationally linked thereto may e.g. be a leader sequence such as the leader sequence derived from WTaMFpp. The expression cassette may e.g. cloned 3' and operationally linked of a GAL10 (galactose-inducible) promoter in the low-copy pRS314 yeast/*Escherichia coli* shuttle vector (ATCC Manassas, Va., USA) to create a panel of vectors with different secretory leaders and BAP orientations. All vectors may e.g. contain a cloning site flanked by KpnI and MluI restriction sites, which facilitate the introduction of the POI between the acTEV/BAP and FLAG tags. The host strain (derived from 13.15464a) expresses the *E. coli* BirA biotin ligase responsible for ligating biotin onto the BAP tag. BirA (Codon Devices, Inc.) carries the C-terminal his-asp-glu-leu (SEQ ID NO: 12) endoplasrnic reticulum retention signal sequence and is directed to the secretory pathway by being fused to the yeast invertase secretory leader and expressed under the control of the cytochrome c (CYC1) promoter. Protein disulfide isomerase (PDI) is co-expressed under the control of the ADH1 promoter. The BirA and PDI genes may be e.g. cloned into the pRS306 and pRS305 vectors, respectively (ATCC), which may e.g. then be stably integrated into the yeast chromosome to produce the JAC100H SECANT surface display strain (mat a, trp1, pep4::HIS3, Dpdb1, ADH-PDI::LEU2, CYC1-BirA::URA3). Transformation of the yeast cells may e.g. be done by the method according to Benatuil et al. (2011) Protein Engineering, Design & Selection Vol. 23, 4:155-159 as outlined in the appended examples, or e.g. according to Rakestraw et al, e.g. as follows: The EZ Yeast Transformation Kit (Zymo Research, Orange, Calif., USA) may be used used to transform the JAC100H display strain with SECANT vectors containing the inventive polynucleotides. Transformants may then be selected on SC glucose, Trp2 plates (Teknova, Hollister, Calif., USA) for 2 days at 308C. A single colony may then be picked and inoculated into 5 ml synthetic dextrose casein amino acids (SD-CAA) media supplemented with biotin (2% glucose, 0.67% yeast nitrogen base, 0.54% $Na_2HPO_4$, 0.86% $NaH_2PO_4$. $H_2O$, 0.5% casein amino acids and 2.5 mg/l biotin) and may e.g. be grown overnight at 30° C. Once the culture has e.g. grown to OD600 ~0.5; it may be pelleted and then resuspended in 5 ml phosphate-buffered, biotin-supplemented yeast extract, peptone, galactose (YPG) media (2% galactose, 2% peptone, 1% yeast extract, 0.025% bovine serum albumin (BSA), 0.54% $Na_2HPO_4$, 0.86% $NaH_2PO_4$. $H_2O$, and 2.5 mg/l biotin). The culture may then e.g, be shaken for 24 h at 20° C. This incubation in YPG starts the production and biotinylation of the POI and is termed the 'preinduction'.

After pre-induction, $2\times10^7$ cells may be withdrawn for avidination: For example, the cells may be first pelleted and washed three times in 1 ml carbonate buffer (4.2% NaHCO3 and 0.034% Na2CO3, pH ¼ 8.4) before being biotinylated by incubation in 4 mg (40 ml dry volume) 3.4 kDa NHS-PEG-biotin (Laysan Bio, Arab, Ala., USA) dissolved in 40 ml carbonate buffer for 15 min at room temperature. After biotin labeling, the cells may be pelleted and washed three times in 1 ml phosphate-buffered saline (PBS)/BSA (1 mg/ml). After pre-induction, $2\times10^7$ cells may be withdrawn for avidination (FIG. 1b). For example, the cells may e.g. first be pelleted and washed three times in 1 ml carbonate buffer (4.2% NaHCO3 and 0.034% Na2CO3, pH % 8.4) before being biotinylated by incubation in 4 mg (40 ml dry volume) 3.4 kDa NHS-PEG-biotin (Laysan Bio, Arab, Ala., USA) dissolved in 40 ml carbonate buffer for 15 min at room temperature. After biotin labeling, the cells may e.g. be pelleted and washed three times in 1 ml phosphate-buffered saline (PBS)/BSA (1 mg/ml). The cells may then e.g. be washed from the plate by adding 1 ml of PBS/BSA to each well and incubating at room temperature for 2 min. The cells may then e.g. be suspended in the PBS/BSA by pipetting up and down and transferred to a 1.5 ml tube. Any remaining cells may e.g. be collected from the plate with at least one additional application of 1 ml PBS/BSA and then transferred to the 1.5 ml tube. The cells may then e.g. be pelleted, washed three times in 1 ml PBS/BSA and placed on ice. The cells may then e.g. be suspended in 40 µl 20 mg/ml avidin (Sigma) and may be incubated for 10 min at room temperature. Cells that are pre-induced but not labeled with avidin secrete soluble, biotinylated protein directly into the media. After avidination the cells may be pelleted, washed twice in 1 ml PBS/BSA and resuspended in 50 µl PBS/BSA. Twenty-five microliters of the cells may e.g. be inoculated into 1.2 ml of induction media and vortexed thoroughly. Induction media was prepared by passing YPG/BSA (2% galactose, 2% peptone, 1% yeast extract and 0.025% BSA) over an avidin-agarose column (Pierce, Rockford, Ill., USA) to remove the biotin found naturally in the media. Then, 20.6 w/v % (for HSA) or 11 w/v % 8 kDa polyethylene glycol (Sigma) was dissolved in 3 ml of the biotin-filtered media and filter sterilized with a 0.2 µm syringe filter (Becton Dickinson, Franklin Lakes, N.J., USA). Lastly, 100 mg/ml avidin may e.g. be added to a final concentration of 1 mg/mi. After mixing the cells in the induction media, 1.2 ml of the media/cell suspension may e.g. be added to one well of a six-well plate (Becton Dickinson) and incubated at 20° C. or 25° C. for 16 h without shaking. The induction allows the cells to secrete the biotinylated protein that will then be captured by the surface-bound avidin.

In one embodiment, the vNARs of the invention which display an altered affinity to a first antigen compared to a reference sample may e.g. be detected and/or selected by phage display.

As used herein, "phage display" describes an in vitro selection technique in which the vNAR domain according to the invention or e.g. a fusion protein comprising the HV2 domain of the invention, is genetically fused to a coat protein of a bacteriophage, resulting in display of the fused protein on the exterior of the phage virion, while the DNA encoding the fusion protein or peptide resides within the virion. This physical linkage between the displayed protein and the DNA encoding it allows screening of vast numbers of variants of the vNAR HV2 domains of the invention or e.g. fusion proteins comprising the inventive vNAR domains. For example, phage display may be done according to any protocol known in prior art, such as e.g. the protocol of Engberg et al. (1996) Mol Biotechnol. December; 6(3):287-310.

In one embodiment, the vNARs of the invention which display an altered affinity to a first antigen compared to a reference sample are detected and/or selected by mammalian display. For example, any protocol or technology for mammalian yeast display may be utilized in the inventive method, such as e.g. that disclosed in WO 2008/070367 A2. In one embodiment, protein arrays may e.g. also be used for the detectin and/or selection of the inventive vNAR domains, or e.g. of inventive fusion proteins comprising the inventive vNAR domains. The term "protein array" as used in the inventive method refers to a protein array, a protein microarray or a protein nanoarray. A protein array may include, for example, a "ProtoArray™," human protein high density array (Invitrogen Corporation, available on the Internet at Invitrogen.com). The ProtoArray™ high density protein array can be used to screen complex biological mixtures, such as serum, to assay for the presence of autoantibodies directed against human proteins. The term "protein chip" may be used synonymously with protein array in the inventive method. The term "reference sample" as used in the inventive method refers to a at least one or more, e.g. at least 10, 100, $10^3$, $10^4$, $10^5$, or $10^6$ vNAR domains which have not been randomized, or refers to e.g. at least 10, 100, $10^3$, $10^4$, $10^5$, or $10^6$ cells which display on their surface at least one vNAR domain, e.g. 10, 100, $10^3$, $10^4$, $10^5$, or $10^6$ vNAR domains which have not been randomized and in which the binding to the first antigen of interest is unaltered.

In one embodiment the inventive vNAR domain comprises a detectable tag. The term detectable tag as used in the inventive method refers to a moiety which is covalently or non-covalently bound to the inventive vNAR domain. A tag according to the invention may e.g. be a molecule that can be directly (i.e., a primary label) or indirectly (i.e., a secondary label) detected; for example a label can be visualized and/or measured or otherwise identified so that its presence or absence can be known. Exemplary labels include, fluorescent labels (e.g. a green fluorescent protein, a red fluorescent protein, a yellow fluorescent protein, etc.) and label enzymes, or e.g. an optically-detectable label, a partner of a binding pair, and a surface substrate binding molecule (or attachment tag). As will be evident to the skilled artisan, many molecules may find use as more than one type of tag, depending upon how the tag is used. In one embodiment, the tag or label as described below is incorporated into the polypeptide as a fusion protein. The detectable tag according to the invention may e.g. also include polypeptides which are provided as a portion of a chimeric vNAR molecule of the invention comprising a first polypeptide (e.g. the inventive vNAR domain) fused to another, heterologous polypeptide or amino acid sequence. In one embodiment, such a chimeric vNAR molecule comprises a fusion of a first polypeptide with a tag polypeptide. The detectable tag may be comprised of a polypeptide such as FLAG, HIS, Myc, HA, V5 tag, S-tag, SBP-tag, or Strep-tag, or may e.g. comprise protein tags such as e.g., GST-tag, MBP-tag, GFP-tag.

The detectable tag according to the invention may e.g. be present on the inventive vNAR domains or fusion proteins comprising the inventive vNAR domains (e.g. the fusion protein may comprise at least one vNAR domain according to the invention) at the amino- or carboxyl-terminus of the vNAR domain or e.g. fusion protein comprising at least one inventive vNAR domain.

In one embodiment the detection and/or selection of vNAR domains according to the invention comprising the flow cytometry, FACS, ELISA, or microfluidics. The term "selecting" as used within the inventive method refers to the process of identifying and/or isolating vNAR domains, or e.g. fusion proteins comprising one or more vNAR domains of the invention, or e.g. cells which display on their surface the inventive vNAr or e.g. fusion protein comprising one or more vNAR domains of the invention. Selection in the inventive method may comprise various technologies known to the skilled person, such as e.g. immuno-panning (see e.g. Wysocki et al. Proc. Natl. Acad. Sci. USA Vol. 75, No. 6, pp. 2844-2848, June 1978), magnetic-activated cell sorting (MACS), flow-cytometry, fluorescence-activated cell sorting (FACS), or droplet-based microfluidics (see e.g. Mazutis et al., 2013, Nature Protocols 8, 870-891). The selected cells of the invention may as part of the selection e.g. be separated and isolated from host cells that do not display the protein of interest on their surface by the methods as disclosed above. For example, FACS may be used to sort cells into different vials or containers, or MACS may be used to separate host cells that display the protein on their surface, or droplet-based microfluidics may be used to select and isolate host cells according to the invention which display the protein of interest on their surface.

According to one embodiment of the invention, the first antigen of interest may be a cell surface antigen, preferably a cancer cell surface antigen, or cancer cell surface antigens, such as those disclosed above.

In one embodiment, the present invention provides for a fusion protein which comprises the inventive vNAR domain. For example the inventive fusion protein may comprise the a vNAR domain of the following structure FW1-CDR1-FW2-HV2-FW3a-HV4-FW3b-CDR3-FW4, whereby FWx denotes framework x, CDRx complementarity determining region x, HV 2 denotes the inventive HV2 domain, e.g. a randomized HV2 domain according to the invention. The inventive vNAR domain may e.g. be fused a Fc domain. The term "Fc domain" or "Fc region" as used in the inventive method refers to the portion of an immunoglobulin, e.g., an IgG molecule that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor.

The Fc domain comprises the C-terminal half of two heavy chains of an IgG molecule that are linked by disulfide bonds. It has no antigen binding activity but contains the carbohydrate moiety and binding sites for complement and Fc receptors, including the FcRn receptor. "Fc domain" includes for example native sequence Fc regions and variant Fc regions, e.g. such as those disclosed in WO 02/094852), as well as polymorphisms have been observed at a number of positions in Fc domains, including but not limited to positions 270, 272, 312, 315, 356, and 358. Within the inventive method, the term "Fc" can refer to this region in isolation, or this region in the context of an antibody, antibody fragment, or Fc fusion protein.

For example, an IgG Fc region may comprise an IgG CH2 and an IgG CH3 domain. The "CH2 domain" of a human IgG Fc region usually extends from an amino acid residue at about position 231 to an amino acid residue at about position 340, whereby a carbohydrate chain may be attached to the CH2 domain. The "CH3 domain" may comprise the stretch of amino acids C-terminal to a CH2 domain in an Fc region, e.g. from an amino acid residue at about position 341 to an amino acid residue at about position 447 of an IgG. The fusion protein may e.g. also comprise fusions of one or more of the inventive vNAR domains to serum albumin, preferably human serum albumin. The inventive fusion protein may e.g. comprise the vNAR domain as a amino-terminal fusion, or as a carboxy-terminal fusion. For example, the inventive fusion protein may also comprise more than one vNDAR domain, e.g. the inventive fusion protein may comprise two, three, or four inventive vNAR domains, e.g. by fusion to both amino- and carboxy-terminus of the respective fusion protein.

In one embodiment of the present invention, the inventive fusion protein comprises human Fc-domains or sequence variants thereof. Accordingly, the inventive fusion protein may comprise Fc domains as disclosed above, or sequence variants thereof. Sequence variants of the Fc domain of the inventive Fc-vNAR fusion protein are at least 80%, 85%, 90%, 95%, or 98%, or from about 92% to about 98%, e.g. 92%, 93%, 94%, 95%, 96%, 97%, or 98% identical to the Fc domain as disclosed above. Sequence similarity for the inventive Fc fusion protein may be calculated as described above. The sequence similarity may be calculated over the entire length of the amino acid sequences of the Fc domain, but may also be calculated over any part or position of the amino acid sequences of 10-200 amino acids, or 110-190 amino acids, or 120-180 amino acids, or 130-170 amino acids, or 140-160 amino acids, or 10-100 amino acids, or 20-90 amino acids, 30-80 amino acids, 40-70 amino acids, 50-60 amino acids in length, e.g. of about 15-55 amino acids in lengths, or of about 25-115 amino acids in length, or of about 35-95 amino acids in length, or of about 45-85 amino acids in length, or of about 12, 13, 14, 15, 16, 17, 18, 19, 20, 21, 22, 23, 24, 25, 26, 27, 28, 29, 30, 32, 34, 35, 36, 37, 38, 39, 40, 42, 46, 48, 51, 54, 56, 57, 59, or 60 amino acids in length.

For example, sequence identity of the amino acid sequence of the inventive fusion protein or any protein as disclosed in the present invention is defined as the percentage of amino acid residues in a candidate sequence that are identical with the amino acid residues in a protein of interest of the invention, after aligning the sequences and introducing gaps, if necessary, to achieve the maximum percent sequence identity, and not considering any conservative substitutions as part of the sequence identity. Alignment for purposes of determining percent amino acid sequence identity may be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For example, percent sequence identity may also be determined by methods as disclosed in Altschul et al, Bull Math. Bio. 48:603 (1986), and Henikoff and Henikoff, Proc. Natl Acad. Sci. USA 1992 Nov. 15; 89(22):10915-9. Briefly, two amino acid sequences are aligned to optimize the alignment scores using a gap opening penalty of 10, a gap extension penalty of 1, and the "BLOSUM 62" scoring matrix of Henikoff and Henikoff as disclosed below (amino acids are indicated by the standard one-letter codes). The percent identity is then calculated as: ([Total number of identical matches]/[length of the longer sequence plus the number of gaps introduced into the longer sequence in order to align the two sequences])*100).

Math. 25:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRK"), as explained in Appendix 2 of Pearson, Meth. Enzymol. 183:63 (1990).

In one embodiment, the fusion proteins of the invention may comprise fusions of the inventive HV2 domain to VH antibodies, e.g. by an in-frame fusion between CDR2 and CDR3 thereby replacing the beta-folds between CDR2 and CDR3, or e.g. HV2 may be included in the b-folds. The inventive HV2-domain may also by grafted onto other immunoglobulin, such as e.g. IgM type antibodies, or may e.g. be fused to VHH antibodies replacing the VHH domains.

In one embodiment, the inventive fusion protein induces ADCC when bound to a first and second antigen of interest

| | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| Ala | 4 | | | | | | | | | | | | | | | | | | | |
| Arg | -1 | 5 | | | | | | | | | | | | | | | | | | |
| Asn | -2 | 0 | 6 | | | | | | | | | | | | | | | | | |
| Asp | -2 | -2 | 1 | 6 | | | | | | | | | | | | | | | | |
| Cys | 0 | -3 | -3 | -3 | 9 | | | | | | | | | | | | | | | |
| Gln | -1 | 1 | 0 | 0 | -3 | 5 | | | | | | | | | | | | | | |
| Glu | -1 | 0 | 0 | 2 | -4 | 2 | 5 | | | | | | | | | | | | | |
| Gly | 0 | -2 | 0 | -1 | -3 | -2 | -2 | 6 | | | | | | | | | | | | |
| His | -2 | 0 | 1 | -1 | -3 | 0 | 0 | -2 | 8 | | | | | | | | | | | |
| Ile | -1 | -3 | -3 | -3 | -1 | -3 | -3 | -4 | -3 | 4 | | | | | | | | | | |
| Leu | -1 | -2 | -3 | -4 | -1 | -2 | -3 | -4 | -3 | 2 | 4 | | | | | | | | | |
| Lys | -1 | 2 | 0 | -1 | -3 | 1 | 1 | -2 | -1 | -3 | -2 | 5 | | | | | | | | |
| Met | -1 | -1 | -2 | -3 | -1 | 0 | -2 | -3 | -2 | 1 | 2 | -1 | 5 | | | | | | | |
| Phe | -2 | -3 | -3 | -3 | -2 | -3 | -3 | -3 | -1 | 0 | 0 | -3 | 0 | 6 | | | | | | |
| Pro | -1 | -2 | -2 | -1 | -3 | -1 | -1 | -2 | -2 | -3 | -3 | -1 | -2 | -4 | 7 | | | | | |
| Ser | 1 | -1 | 1 | 0 | -1 | 0 | 0 | 0 | -1 | -2 | -2 | 0 | -1 | -2 | -1 | 4 | | | | |
| Thr | 0 | -1 | 0 | -1 | -1 | -1 | -1 | -2 | -2 | -1 | -1 | -1 | -1 | -2 | -1 | 1 | 5 | | | |
| Trp | -3 | -3 | -4 | -4 | -2 | -2 | -3 | -2 | -2 | -3 | -2 | -3 | -1 | 1 | -4 | -3 | -2 | 11 | | |
| Tyr | -2 | -2 | -2 | -3 | -2 | -1 | -2 | -3 | 2 | -1 | -1 | -2 | -1 | 3 | -3 | -2 | -2 | 2 | 7 | |
| Val | 0 | -3 | -3 | -3 | -1 | -2 | -2 | -3 | -3 | 3 | 1 | -2 | 1 | -1 | -2 | -2 | 0 | -3 | -1 | 4 |

For example, additional established algorithms available may be used to align and determine the similarity of two or more amino acid sequences. The "FASTA" similarity search algorithm of Pearson and Lipman is a suitable protein alignment method for examining the level of identity shared by two or more amino acid sequences (see e.g. Pearson and Lipman, Proc. Natl. Acad. Sci. USA &5:2444 (1988), and by Pearson, Meth. Enzymol. 183:63 (1990)). Briefly, FASTA first characterizes sequence similarity by identifying regions shared by the query sequence and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol Biol. 48:444 (1970); Sellers, SIAM J. Appl.

in vivo, e.g. when the bispecific inventive fusion protein is bound to a first and a second antigen on a tumor or cancer cell, e.g. to cancer cell surface antigens as disclosed above. The term ADCC (antibody dependent cell cytotoxicity) as used for the inventive fusion protein refers to a mechanism of cell-mediated immune defense whereby an effector cell of the immune system actively lyses a target cell, whose membrane-surface antigens have been bound by specific antibodies. ADCC is mediated by e.g. the binding of CD16 (FcγRIII) expressed on NK cells to the Fc domain of antibodies (see e.g. Clynes et al. (2000) Nature Medicine 6, 443-446). ADCC may e.g. be improved by amino acid substitutions in the Fc domain which affect the binding of the Fc domain to CD16. For example, Shields et al. (J Biol Chem 9(2), 6591-6604 (2001)) showed that amino acid substitutions at positions 298, 333, and/or 334 of the Fc region (EU numbering of residues) improve ADCC. Alternatively, increased Fc receptor binding and effector function may e.g. be obtained by altering the glycosylation of the Fc region. The two complex biantennary oligosaccharides attached to Asn 297 of the Fc domain are typically buried between the CH2 domains, forming extensive contacts with the polypeptide backbone, and their presence is essential for the antibody to mediate effector functions including ADCC (Lifely et al., Glycobiology 5, 813-822 (1995); Jefferis et al., Immunol Rev 163, 59-76 (1998); Wright and Morrison, Trends Biotechnol 15, 26-32 (1997)). Overexpression of e.g.

β(1,4)-N-acetylglucosaminyltransferase III (GnTIII), a glycosyltransferase catalyzing the formation of bisected oligosaccharides, significantly increases the in vitro ADCC activity of antibodies. Thus overexpression of e.g. of GnTIII in cell lines used for the production of the inventive fusion protein, may result in inventive fusion proteins enriched in bisected oligosaccharides, which are generally also non-fucosylated and may exhibit increased ADCC.

ADCC of the inventive fusion protein may e.g. be further augmented by additionally overexpressing mannosidase II (Mann) in addition to GnTIII in host cell, or cell lines, as the resulting inventive fusion protein may be enriched in bisected, non-fucosylated oligosaccharides of the complex type (see e.g. Ferrara et al., Biotechn Bioeng 93, 851-861 (2006)). For example, the elimination of fucose from the innermost N-acetylglucosamine residue of the oligosaccharide core present in the inventive Fc fusion protein may also increase ADCC activity (see e.g. Shinkawa et al., J Biol Chem 278, 3466-3473 (2003)), thus the inventive Fc fusion protein may also e.-g. produced in a host cell, or cell line with reduced fucosylation, by e.g. expression in α(1,6)-fucosyltransferase deficient host cells (see e.g. Yamane-Ohnuki et al., Biotech Bioeng 87, 614-622 (2004); Niwa et al., J Immunol Methods 306, 151-160 (2006)).

In one embodiment the present invention provides a vNAR obtainable by the inventive method, e.g. a vNAR as disclosed above which may be a vNAR type I, II, or type IV as disclosed above. In one embodiment the present invention also provides polynucleotides or vectors encoding the inventive vNAR or vNAR fusion proteins as disclosed above. The term vector or expression vector used for the inventive method or for the inventive fusion proteins refers to a nucleic acid molecule capable of extra-chromosomal replication. Preferred vectors are those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. Nucleic acid sequences necessary for expression of the inventive fusion protein or inventive vNAR in eukaryotic cells comprise e.g. at least one promoter, and enhancers, termination and polyadenylation signals as well as a selectable marker, such as e.g. an antibiotic resistance. Expression vectors which may be used for expression of the inventive vNAR or vNAR fusion proteins may e.g. comprise pCMV, pcDNA, p4X3, p4X4, p4X5, p4X6, pVL1392, pVL1393, pACYC177, PRS420, or if viral based vector systems are to be used e.g. pBABEpuro, pWPXL, pXP-derived vectors.

In one embodiment, the present invention provides a host cell which comprises the polynucleotide sequence or vector as disclosed above, e.g. a polynucleotide or vector or expression vector which comprises a coding sequence for the inventive vNAR or the inventive fusion protein as disclosed above. For example, a host cell for use in the invention may be a yeast cell, insect cell or mammalian cell. For example, the host cell of the invention may be an insect cell selected from Sf9, Sf21, S2, Hi5, or BTI-TN-5B1-4 cells, or e.g. the host cell of the invention may be a yeast cell selected from *Saccharomyces cerevisiae, Hansenula polymorpha, Schizosaccharomyces pombe, Schwanniomyces occidentalis, Kluyveromyceslactis, Yarrowia lipolytica* and *Pichia pastoris*, or e.g. the host cell of the invention may be a mammalian cell selected from HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, and D-17.

In one embodiment, the present invention provides a method for producing inventive vNAR or vNAR fusion proteins as disclosed herein, whereby the inventive method comprises the steps of culturing at least one host cell of the invention as disclosed above under conditions sufficient for protein expression of the inventive vNAR, or vNAR fusion protein, and isolating and purifying the inventive vNAR protein, or vNAR fusion protein. For example, host cells of the invention may be allowed to grow in DMEM containing 10% FBS, and were incubated at 37° C. in 10% $CO_2$, or e.g. in protein-free culture medium to aid in the subsequent isolation and purification, or e.g. in Grace's insect medium, express Five® SFM (Life Technologies), or High Five medium (Life Technologies), YNM medium, YPD broth, or e.g. PichiaPink (Life technologies).

The host cells of the invention may e.g. be allowed to grow between 12-408 h, e.g. for about 12 to about 400 h, e.g. between 14 h, 16 h, 18 h, 20 h, 24 h, 36 h, 48 h, 72 h, 96 h to about 120 h, 144 h, 168 h, 192, 216 h, 240 h, 264 h, 288 h, 312 h, 336 h, 360 h, 384 h, 408 h. Subsequently, the inventive vNAR or inventive fusion protein may be isolated and purified. For example, the protein of the invention may be purified and isolated by chromatography, e.g. ion-exchange chromatography, size-exclusion chromatography, ammonium sulfate precipitation, or ultrafiltration. For example, the inventive vNAR or inventive fusion proteins may also comprise a signal sequence, which refers to an amino acid sequence which is capable of initiating the passage of a polypeptide, to which it is operably linked, e.g. by a peptide bond, into the endoplasmic reticulum (ER) of a host cell. The signal peptide is generally cleaved off by an endopeptidase (e.g. a specific ER-located signal peptidase) to release the (mature) polypeptide. The length of a signal peptide is typically in the range from about 10 to about 40 amino acids.

In one embodiment the present invention also provides a polynucleotide library which comprises a plurality of polynucleotides encoding the HV2 domain of the invention. The term "polynucleotide library", or "plurality of polynucleotides" of the invention denotes a library or collection of at least two different DNA sequences which at least encode the inventive HV2 domain, or e.g. which encode one of vNAR type I, II or type IV comprising the inventive HV2 domain. For example, the polynucleotide library comprises at least 1000 different DNA sequences, more preferably at least $10^4$, $10^5$, $10^6$, or at least 100, 1000, or from about $10^3$ to about $10^7$ different DNA sequences encoding the inventive HV2 domain. Preferably, the polynucleotide library of the invention comprises a plurality of polynucleotides encoding type I, II, or type IV vNAR domains of the overall structure FW1-CDR1-FW2-HV2-FW3a-HV4-FW3b-CDR3-FW. In one embodiment the present invention provides to bispecific vNAR molecules according to SEQ ID NO: 2, SEQ ID NO: 4, SEQ ID NO: 5.

In one embodiment, the present invention pertains to the use of the inventive vNAR or inventive vNAR fusion proteins in the manufacture of a medicament. Accordingly, the inventive vNAR proteins or inventive vNAR fusion proteins may e.g. be used in the manufacture of a medicament, e.g. formulated to be administered to an individual in need thereof. The inventive medicament of the invention may e.g. be an injectable liquid, capsule, lozenge, freeze-dried formulation for reconstitution and may comprise e.g. from about 0.01 mg/ml to about 25 mg/ml of the inventive vNAR protein or inventive vNAR fusion protein, or from about 0.02 mg/ml to about 20 mg/ml, or from about 0.075 mg/ml to about 17.5 mg/ml, or from about 0.1 mg/ml, 0.25 mg/ml, 0.5 mg/ml, 0.75 mg/ml, 1 mg/ml, 1.5 mg/ml, 2 mg/ml, 2.5 mg/ml, 3 mg/ml, 3.5 mg/ml, 3.75 mg/ml, 4 mg/ml, 4.25 mg/ml, 4.5 mg/ml, 5 mg/ml, 5.5 mg/ml, 6 mg/ml, 6.5 mg/ml, 7 mg/ml, 7.5 mg/ml, 8 mg/ml, 9 mg/ml, 9.5 mg/ml, 10 mg/ml, 10.5 mg/ml, 11 mg/ml, 11.5 ml/ml, 12 mg/ml, 12.5 mg/ml, 12.75 mg/ml, 13 mg/ml, 14 mg/ml, 14.5 mg/ml, 15 mg/ml to about 16 mg/ml, 17 mg/ml, 18 mg/ml, 19 mg/ml, 20 mg/ml, 21 mg/ml, 22 mg/ml, 23 mg/ml, 24 mg/ml, 25 mg/mlm, or e.g. from about 26 mg/ml to about 50 mg/ml, e.g. 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, or e.g. 0.001 mg/ml to about 0.009 mg/ml.

In one embodiment the invention provides a pharmaceutical composition which comprises the inventive vNAR or vNAR fusion protein as disclosed above and a pharmaceutical acceptable carrier or diluent. In the context of the pharmaceutical composition of the invention a pharmaceutically-acceptable carrier refers to a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include e.g. sugars, such as lactose, glucose and sucrose; or e.g. starches, such as corn starch and potato starch; or e.g. cellulose, and its derivatives, such as sodium carboxymethyl cellulose, ethyl cellulose and cellulose acetate; or e.g. gelatin; or e.g. excipients, such as cocoa butter and suppository waxes; or e.g. oils, such as peanut oil, cottonseed oil, safflower oil, sesame oil, olive oil, corn oil and soybean oil; or e.g. glycols, such as propylene glycol; or e.g. polyols, such as glycerin, sorbitol, mannitol and polyethylene glycol; or e.g. esters, such as ethyl oleate and ethyl laurate; or e.g. the following may also be used: isotonic saline or buffered (aqueous) solutions, e.g phosphate, citrate, etc. buffered solutions, an aqueous buffered solution, containing e.g. a sodium salt, preferably at least 50 mM of a sodium salt, a calcium salt, preferably at least 0.01 mM of a calcium salt, and/or a potassium salt, preferably at least 3 mM of a potassium salt. According to a preferred embodiment, the sodium, calcium and/or potassium salts may occur in the form of their halogenides, e.g. chlorides, iodides, or bromides, in the form of their hydroxides, carbonates, hydrogen carbonates, or sulfates, etc. Without being limited thereto, exam-pies of sodium salts include e.g. NaCl, NaI, NaBr, $Na_2CO_3$, $NaHCO_3$, $Na2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the composition of the invention. According to a more preferred embodiment, the composition of the invention suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. The composition of the invention may be hypertonic, isotonic or hypotonic with reference to the specific reference medium, i.e. the pharmaceutical composition of the invention may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as ref-erence media in "in vitro" methods, such as common buffers or liquids. Such common buffers or liquids are known to a skilled person.

In one embodiment the present invention pertains to a method of treatment of an individual in need thereof afflicted with a pathological condition comprising administering the person in need thereof the inventive pharmaceutical composition as disclosed above. For example, the inventive method of treatment may comprise administering a person in need thereof afflicted with a pathological condition from about 0.001 mg/kg to about 50 mg/kg of the inventive pharmaceutical composition, or from about 0.005 mg/kg to about 45 mg/kg, or from about 0.01 mg/kg to about 40 mg/kg, or from about 0.05 mg/kg to about 35 mg/kg, or from about 0.1 mg/kg, 0.5 mg/kg, 0.75 mg/kg, 1 mg/kg, 1.5 mg/kg, 2 mg/kg, 2.5 mg/kg, 3 mg/kg, 4 mg/kg, 5 mg/kg, 6 mg/kg 7 mg/kg, 8 mg/kg, 9 mg/kg, 10 mg/kg, 12.5 mg/kg, 15 mg/kg, 17.5 mg/kg, 20 mg/kg, 22.5 mg/kg, 25 mg/kg to about 26 mg kg/, 27 mg/kg, 28 mg/kg, 29 mg/kg, 30 mg/kg, 32.5 mg/kg, 35 mg/kg, 37.5 mg/kg, 40 mg/kg, 42.5 mg/kg, 45 mg/kg. As used the term "mg/kg" refers to mg of the inventive pharmaceutical composition/kg body weight in the present invention. The pathological conditions which may be treated by the inventive method may be cancer, autoimmune disease, or viral infection. The term "cancer"', as used within the context of the inventive method of treatment, refers to a variety of conditions caused by the abnormal, uncontrolled growth of cells, e.g. cells capable of causing cancer, referred to as "cancer cells", possess characteristic properties such as uncontrolled proliferation, immortality, metastatic potential, rapid growth and proliferation rate, and/or certain typical morphological features. Cancer cells may e.g. be in the form of a tumor, but such cells may also exist singly within a subject, or may be a non-tumorigenic cancer cell. The term cancer as used in the context of the inventive method of treatment may e.g. refer to prostate cancer, breast cancer, adrenal cancer, leukemia, lymphoma, myeloma, Waldenström's macroglobulinemia, monoclonal gammopathy, benign monoclonal gammopathy, heavy chain disease, bone and connective tissue sarcoma, brain tumors, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer. Within the context of the inventive method of treatment, the term autoimmune disease may e.g. refer to systemic lupus erythematosis (SLE), Graves disease, type I and type II diabetes, multiple sclerosis, Sjogren syndrome, scleroderma, glomerulonephritis, transplant rejection, e.g., organ and tissue allograft and xenograft rejection and graft versus host disease. The term "viral infection" as used within the context of the inventive method of treatment refers to an abnormal state or condition characterized by viral transformation of cells, viral replication and proliferation, such as e.g. infection by viruses of the herpes family, varicella zoster virus (VZV), Epstein-Barr virus (EBV), cytomegalovirus (CMV), and the like. According to a preferred embodiment, the individual to be treated by the inventive method as disclosed herein is a human.

In one embodiment the present invention provides a kit of parts which comprises the inventive vNAR or vNAR fusion protein as disclosed above and means for detection. Accordingly, the inventive kit of parts may e.g. comprise the inventive vNAR or vNAR fusion protein in a stable form such as e.g. lyophilized or as a liquid formulation such that the inventive vNAR or vNAR fusion protein is sufficiently stable for storage, e.g. for storage at 4° C.-10° C., or ambient temperature for e.g. at least 1-12 weeks, or e.g. at least 1-6 months, or e.g. for at least 2-12 months, e.g. 1, 2, 3, 4, 5, 6, 7, 8, 9, 10, or 11 months. The inventive kit may further comprise means for detection of the inventive vNAR protein or inventive vNAR fusion proteins, such as e.g. quantum dots, detectably labeled antibodies, such as antibody-enzyme complexes, or antibodies coupled to a fluorescent label.

The term quantum dot as used in the context of the inventive kit or in the context of the inventive method as disclosed above refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the CRC Handbook of Chemistry and Physics, 83rd ed., Lide, David R. (Editor), CRC Press, Boca Raton, Fla. (2002)). Quantum dots are known in the art, as they are described in references, such as Weller, Angew. Chem. Int. Ed. Engl. 32: 41-53 (1993), Alivisatos, J. Phys. Chem. 100: 13226-13239 (1996), and Alivisatos, Science 271: 933-937 (1996). Quantum dots may e.g. be from about 1 nm to about 1000 nm diameter, e.g. 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, preferably at least about 2 nm to about 50 nm, more preferably QDs are at least about 2 nm to about 20 nm in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than. the bandgap energy of the core material and may be chosen to have an atomic spacing close to that of the "core" substrate. The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

The term "fluorescent label", or "fluorescent dye", or "fluorophore" which may e.g. be used in the inventive kit for labeling an antibody, which may be used to detect the inventive vNAR or vNAR fusion protein refers to moieties that absorb light energy at a defined excitation wavelength and emit light energy at a different wavelength. Examples of fluorescent labels that may be used in the invention include, but are not limited to: dansyl chloride, dapoxyl, dialkylaminocoumarin, rhodamine isothiocyanate, Alexa 350, Alexa 430, Alexa Fluor 488, Alexa Fluor 532, Alexa Fluor 546, Alexa Fluor 568, Alexa Fluor 594, Alexa Fluor 633, Alexa Fluor 660, Alexa Fluor 680, AMCA, aminoacridine, BODIPY 630/650, BODIPY 650/665, BODIPY-FL, BODIPY-R6G, BODIPY-TMR, BODIPY-TRX, BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy coumarin, Naphtho fluorescein, Oregon Green 488, Oregon Green 500, Oregon Green 514, Pacific Blue, PyMPO, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, fluorescein, HEX, 6-JOE, NBD (7-nitrobenz-2-oxa-I,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, TAMRA, TET, TRIT (tetramethyl rhodamine isothiol), Tetramethylrhodamine, or Texas Red. For example, the inventive kit may be used to detect cancer cell surface antigens as disclosed above in a sample such as e.g. a tissue biopsy, or paraffin section, tissue culture, or body fluid. The sample may e.g. be derived from a patient suffering from a pathological condition, whereby obtaining the sample from the patient does not form part of the of present invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

EXAMPLES

Example 1: SOE PCR for Fragment Generation for Yeast Display

Figure 11:
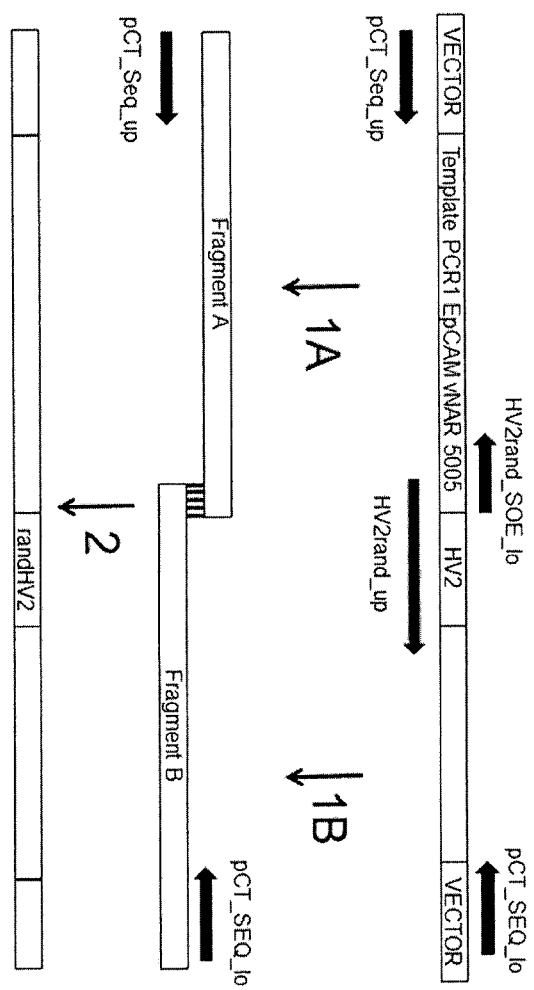
FIG. 11: SOE-PCR scheme for the construction of the insert with randomized HV2. Insert fragment was generated in a 2 step PCR. In the first step, the vNAR-fragment was amplified up to the 5' end of HV2 (1A). In a second step, HV2 was randomized using the HV2rand_up primer. This resulted in a fragment starting at the 5' end of HV2 coding region to the 3' end of the vNAR molecule coding region. In the second PCR, the two fragments act as primer for themselves, to result in full length randomized HV2 vNAR insert to yield primer. After 6 cycles Primer were added to generate sufficient amounts of full length insert.

For the generation of the insert fragment for yeast surface display, plasmid DNA from EpCAM-specific binder 5005 was used as starting material. Two PCR reactions were carried out in parallel to generate two DNA-fragments that were used as starting material for the 3rd PCR (see FIG. 11). PCR-conditions were as followed: 92° C. for 30 sec, [92° C. for 30 sec, 52° C. 30 sec, 72° C. 30 sec]×30 followed by 72° C. for 5 min. For the 3rd PCR, Fragment A and Fragment B (see FIG. 11) were mixed in a molar 1:1 ratio (approx. 50 ng each) and used as template. After 6 cycles of the aforementioned PCR-run, oligonucleotides pCT_Seq_up and pCT_Seq_lo were added to yield the final PCR product with a randomized HV2 coding region, which was used as insert material for the library generation.

Example 2: Library Generation

For generation of yeast libraries bearing a high sequence diversity the transformation of *S. cerevisiae* was performed according to the protocol of Benatuil et al., Protein Eng Des Sel 2010; 23:155-9. Using an overnight culture of *S. cerevisiae* strain EBY 100, 100 mL YPD medium was inoculated to an OD600=0.3, incubation was continued until a cell density of OD600=1.6 was reached. Cells were separated from the media via centrifugation at 3000 rpm for 5 min. In the further progress cells were washed twice with 50 ml ice-cold water and one time with electroporation buffer, followed by conditioning of the yeast cells for 30 min in 20 ml lithium buffer at 30° C. shaking at 180 rpm. After one last washing step with electroporation buffer the cell pellets were resuspended in 100-200 μl electroporation buffer resulting in a final volume of 1 ml and kept on ice.

For each electroporation reaction 1 μg of digested vector backbone and 3 μg of DNA insert were mixed with 400 μl electrocompetent cells in a cold transformation cuvette. Immediately after the electroporation (U=2.5 kV; C=25 μF; R<200Ω; time pulse=5 ms) 8 ml of 1:1 mix 1 M sorbitol: YPD medium was added followed by incubation at 30° C. for 1 h at 180 rpm. After a last centrifugation step cells were resuspended in SDCAA medium and incubated for two days. By streaking out serially diluted cells on SDCAA plates the library size could be determined from the colony counts after three days. The cell culture and preparation was proportionally scaled up if more electrocompetent cells were needed to make larger libraries.

SGCAA medium: 2% (w/v) galactose, 0.17% (w/v) yeast nitrogen base, 0.5% (w/v) casamino acids, 0.5% (w/v) ammonium sulfate, 10% w/v polyethylene glycol 8000, 38 mM Na2HPO4, 62 mM NaH$_2$PO$_4$.H$_2$O [pH 7.4].

Example 3: Induction of Gene Expression in *S. cerevisiae*

Yeast cells transformed with the pCT vector (see Example 2) were used for cell sorting experiments. Because the shark antibody variants were encoded in the vector under control of a galactose promotor, induction of gene expression could be performed by changing the media from glucose-containing media to galactose-containing SGCAA media. Therefore the cells of a corresponding volume of a yeast overnight culture was sedimented (14000 U/min; 2 min) and used to inoculate 50-1000 ml SGCAA medium in a shake-flask to a cell density of OD600=0.5 for an incubation time of at least 1 day at 20° C.

SGCAA medium: 2% (w/v) galactose, 0.17% (w/v) yeast nitrogen base, 0.5% (w/v) casamino acids, 0.5% (w/v) ammonium sulfate, 10% w/v polyethylene glycol 8000, 38 mM Na2HPO4, 62 mM NaH$_2$PO$_4$.H$_2$O [pH 7.4].

Example 4: Cell Staining for FACS and FACS Analysis

Yeast cells were grown overnight in SGCAA medium and pelleted and washed once with PBS. Afterwards cells were incubated in an adequate volume of 1 μM EpCAM. After 15 minutes, cells were again washed with PBS and CDR-Biotin was added (1 μM). After incubation for 30-60 min, cells were washed again. EpCAM-binding was detected using and PE-labeled anti-EpCAM-antibody. CD3ε-binding was detected using either biotinylated CD3ε and Streptavidin-APC or using his-tagged CD3ε and a AlexaFlur-labeled penta-his-antibody ("penta-his" disclosed as SEQ ID NO: 13). Incubation with secondary agents were carried out for 5 minutes on ice. After a repeated wash with PBS the yeast cells were subjected for two dimensional FACS sorting (dimension A: EpCAM-binding; dimension B: CDR-binding). Akin to this, screening was also carried out to select bispecific binders against EpCAM and human Fc. Here EpCAM binding was detected using his-tagged EpCAM and AlexaFlur-labeled penta-his-antibody ("penta-his" disclosed as SEQ ID NO: 13). Binding to human Fc was detected using an PE-labeled anti-human antibody.

Fluorescent-Activated Cell Sorting

Fluorescent-activated cell sorting was performed using a MoFlo Cytomation device and analyzed via Summit 4.3. This device enables measuring the fluorescence of droplets containing single cells. Parallel measurement of fluorescence intensities of vNAR surface presentation on single yeast cells and target protein binding was possible through the use of two lasers emitting light at 488 nm and 640 nm. Before starting the cell sorting procedure, the lasers of the sorting device were adjusted using fluorescently labelled beads. Furthermore a drop-delay was performed in order to determine the position of the cell-containing droplet that should be analyzed. For each sorting round sorting gates were set that define the fluorescence properties of the cells that should be sorted out. Setting of sort gates typically allowed 0.1% false-positive cells as judged by control staining in the absence of antigen.

Parameters of the MoFlo device used in this work for cell sorting experiments:
Side Scatter: 650 (LIN mode)
FL1: 650 (Log mode)
FL2: 600 (Log mode)
FL3: 640 (Log mode)
Charge of plates: 2,500 V
Event rate 5,000-30,000 events/s
Sample pressure: 60.1 psi
Sheath pressure: 59 psi
Nozzle diameter: 70 μm
Sort mode: Sort Purify 1

After cell sorting the sorting efficiency was determined by analyzing a small part of the already sorted cells. Afterwards cells were grown on SDCAA plates for 2 days at 30° C. and used subsequently to induce cell surface presentation for the following sorting round. After incubation on plates for each sorting round a 10 fold excess of cells that were sorted out were suspended in 10% glycerol for cryopreservation.

Figure 6:
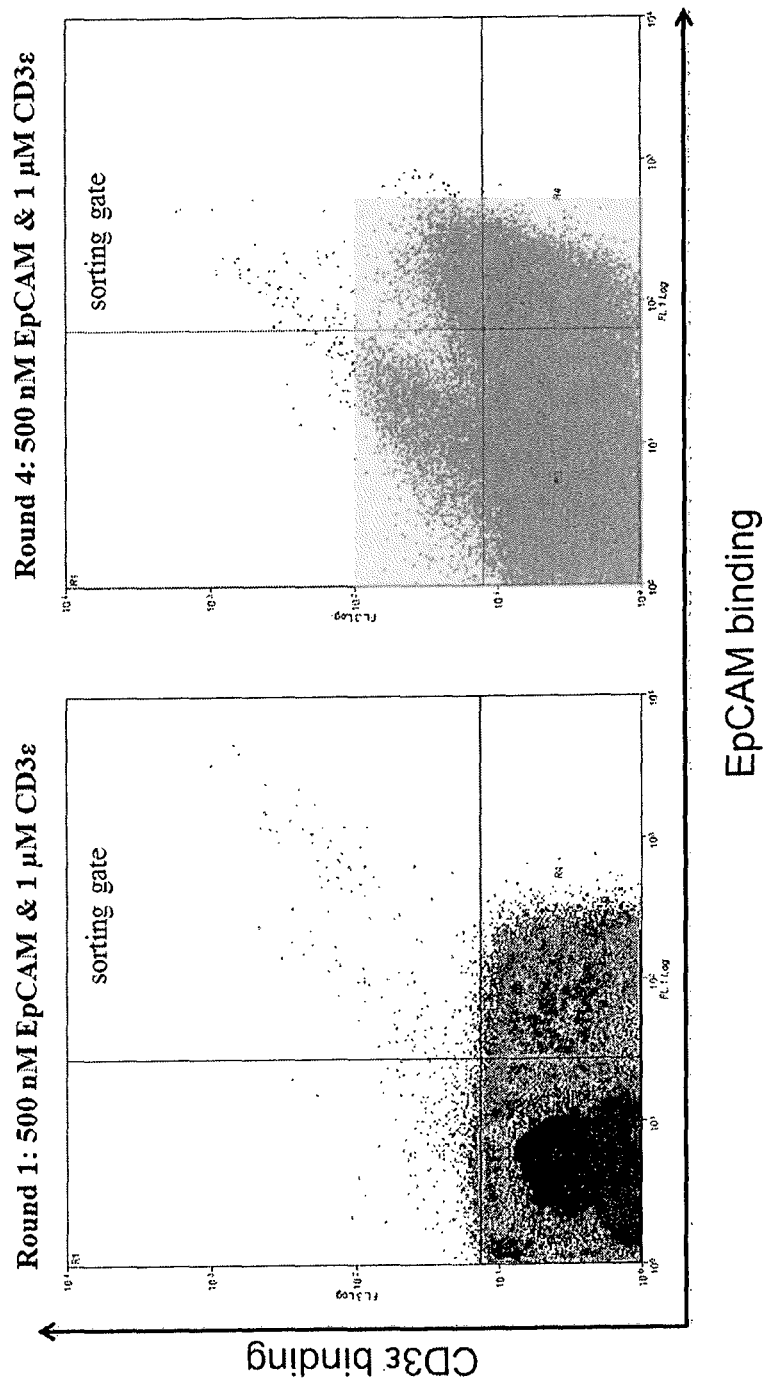
FIG. 6: Library screening for simultaneous binding of EpCAM and CD3ε. Sorting was performed two-dimensional. Round 1 and Round 4 of library screening, sorting gates as well as target concentrations are shown.
Figure 9:
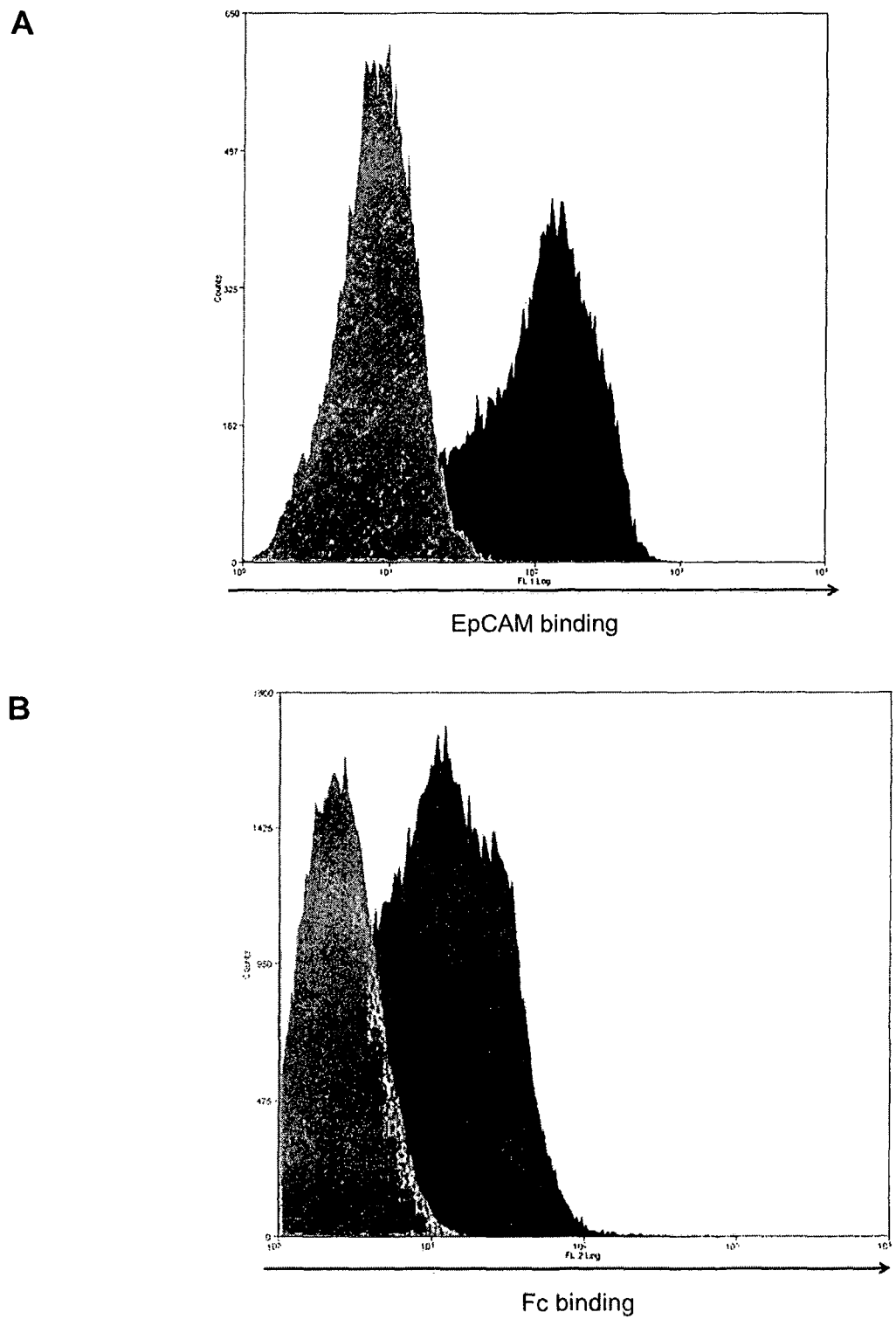
FIG. 9: (A) Validation of bispecificity using yeast surface display. Yeast cells expressing vNAR F1 on their surface incubated with 540 nM EpCAM (black) or only with secondary detection reagents (grey), (B) Validation of bispecificity using yeast surface display. Yeast cells expressing vNAR F1 on their surface incubated with approx. 500 nM Fc-fragment (black) or only with secondary detection reagents (grey).
Figure 10:
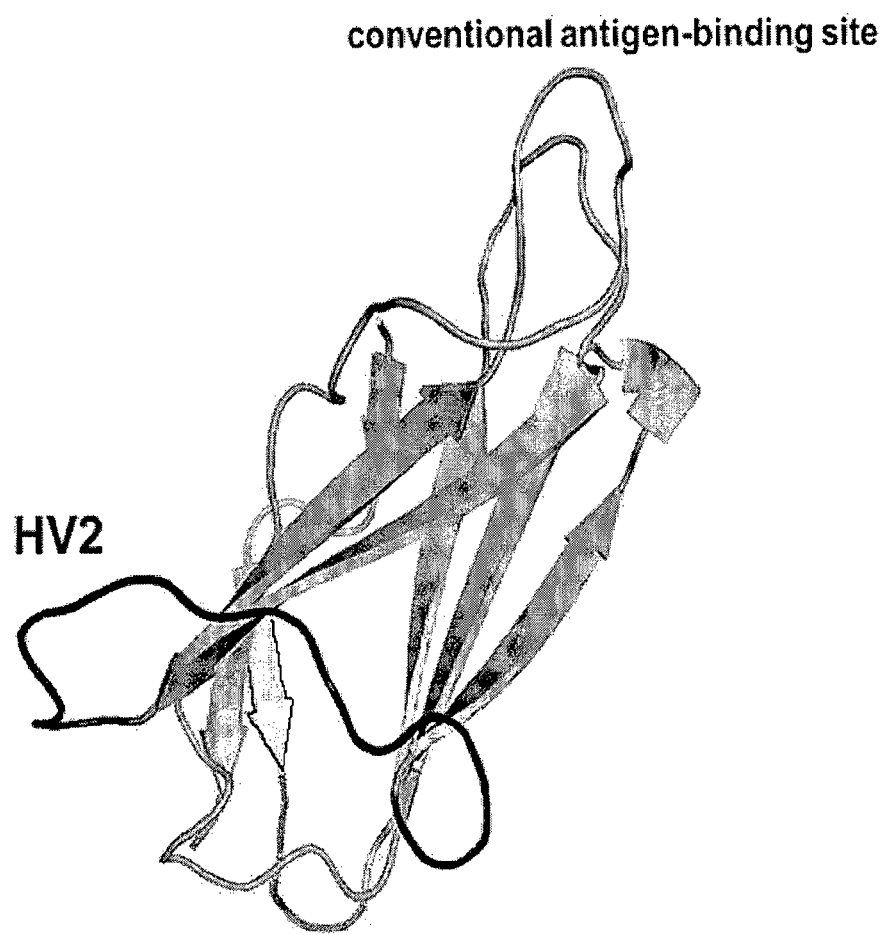
FIG. 10: Model of a vNAR domain surface exposed loop HV2 comprising residues 43-56 of the vNAR domain of the bamboo shark (Chiloscyllium plagiosum); residue numbers differ depending on the species and vNAR type.

The SDCAA medium used comprised: 2% (w/v) glucose, 0.17% (w/v) yeast nitrogen base, 0.5% (w/v) casamino acids, 0.5% (w/v) ammonium sulfate, 38 mM Na$_2$HPO$_4$, 62 mM NaH$_2$PO$_4$.H$_2$O [pH 7.4]. The FACS results are shown in FIGS. 6, 7, and 9.

The invention claimed is:

1. A method for generating bi-specific shark variable antibody domains (vNAR domains) having the structure of FW1-CDR1-FW2-HV2-FW3a-HV4-FW3b-CDR3-FW4, the method comprising:
   (a) randomizing at least one polynucleotide sequence encoding hypervariable region 2 (HV2);
   (b) detecting vNAR domains in which HV2 binds to a first antigen of interest with altered affinity compared to a reference sample and a second antigen of interest is specifically bound by a paratope formed by CDR3 and CDR1; and
   (c) selecting vNAR domains of (b).

2. The method of claim 1, wherein the vNAR domains are one of vNAR type I, vNAR type II, or vNAR type IV.

3. The method of claim 2, wherein randomization of the polynucleotide coding region of HV2 comprised on at least one polynucleotide encoding said vNAR comprises codon-based randomization, NNB randomization, NNK randomization, NNS randomization, or biased-randomization.

4. The method of claim 3, wherein the polynucleotide sequence encoding the HV2 domain comprises the nucleotide sequence $NNN_1(NNN)_7NNN_9$ (SEQ ID NO: 1), wherein
   50% of the codons in position 1 code for the amino acid lysine and the remaining 50% encode any amino acid except cysteine;
   Codons 2-8 may encode any amino acid; and
   50% of the codons in position 9 code for the amino acid threonine, and the remaining 50% encode any amino acid except cysteine.

5. The method of claim 4, wherein vNARs that display an altered affinity to a first antigen compared to a reference sample are detected and/or selected by one of yeast surface display, phage display, mammalian display, or protein array.

6. The method of claim 5, wherein the vNAR further comprises a detectable tag, wherein said detectable tag is located at the amino terminus and/or carboxy-terminus of the vNAR.

7. The method of claim 5, wherein the detection and/or selection of said vNAR is done by flow cytometry, FACS, ELISA, or microfluidics.

8. The method of claim 1, wherein the first and second antigen of interest are cell surface antigens or cancer cell surface antigens.

9. A method of producing a vNAR protein comprising a bi-specific shark variable antibody domain (vNAR domain), the method comprising:
   (a) generating a bi-specific shark variable antibody domain (vNAR domain) having the structure FW1-CDR1-FW2-HV2-FW3a-HV4-FW3b-CDR3-FW4 according to the method of claim 1;
   (b) culturing at least one host cell under conditions sufficient to express a vNAR protein, the host cell comprising a vector encoding the vNAR protein comprising the vNAR domain generated under (a); and
   isolating and purifying said vNAR protein.

* * * * *